US008389473B2

(12) United States Patent
Hathaway et al.

(10) Patent No.: US 8,389,473 B2
(45) Date of Patent: *Mar. 5, 2013

(54) TREATMENT OF CARDIAC ARRHYTHMIAS

(75) Inventors: David R. Hathaway, Lincoln, NE (US); Alain D. Baron, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 8 days.

This patent is subject to a terminal disclaimer.

(21) Appl. No.: 12/750,575

(22) Filed: Mar. 30, 2010

(65) Prior Publication Data

US 2011/0178014 A1    Jul. 21, 2011

Related U.S. Application Data

(62) Division of application No. 10/740,146, filed on Dec. 17, 2003, now Pat. No. 7,790,681.

(60) Provisional application No. 60/434,508, filed on Dec. 17, 2002, provisional application No. 60/434,888, filed on Dec. 19, 2002.

(51) Int. Cl.
*A61K 38/16* (2006.01)
*A61K 38/28* (2006.01)

(52) U.S. Cl. .................. 514/7.2; 424/198.1; 530/308

(58) Field of Classification Search .................. None
See application file for complete search history.

(56) References Cited

U.S. PATENT DOCUMENTS

| | | | |
|---|---|---|---|
| 5,118,666 A | 6/1992 | Habener | |
| 5,120,712 A | 6/1992 | Habener | |
| 5,254,372 A | 10/1993 | Nichols | |
| 5,424,286 A | 6/1995 | Eng | |
| 5,512,549 A | 4/1996 | Chen et al. | |
| 5,545,618 A | 8/1996 | Buckley et al. | |
| 5,574,008 A | 11/1996 | Johnson et al. | |
| 5,670,360 A | 9/1997 | Thorens | |
| 5,705,483 A | 1/1998 | Galloway et al. | |
| 5,846,747 A | 12/1998 | Thorens et al. | |
| 5,981,488 A | 11/1999 | Hoffmann | |
| 6,051,689 A | 4/2000 | Thorens | |
| 6,251,926 B1 | 6/2001 | Momose et al. | |
| 6,268,343 B1 | 7/2001 | Knudsen et al. | |
| 6,284,725 B1 | 9/2001 | Coolidge et al. | |
| 6,451,974 B1 | 9/2002 | Hansen | |
| 6,451,987 B1 | 9/2002 | Staby | |
| 6,458,924 B2 | 10/2002 | Knudsen et al. | |
| 6,514,500 B1 | 2/2003 | Bridon et al. | |
| 6,528,486 B1 | 3/2003 | Larsen et al. | |
| 6,569,832 B1 | 5/2003 | Knudsen et al. | |
| 6,593,295 B2 | 7/2003 | Bridon et al. | |
| 6,706,689 B2 | 3/2004 | Coolidge et al. | |
| 6,833,381 B2 | 12/2004 | Ikeya et al. | |
| 6,867,184 B2 | 3/2005 | Treadway | |
| 6,949,555 B2 | 9/2005 | Guitard et al. | |
| 6,956,026 B2 | 10/2005 | Beeley et al. | |
| 7,084,243 B2 | 8/2006 | Glaesner et al. | |
| 2001/0016586 A1 | 8/2001 | Guitard et al. | |
| 2002/0107206 A1 | 8/2002 | Coolidge et al. | |
| 2002/0137666 A1 | 9/2002 | Beeley et al. | |
| 2002/0146405 A1 | 10/2002 | Coolidge et al. | |
| 2003/0087820 A1 | 5/2003 | Young et al. | |
| 2003/0144206 A1 | 7/2003 | Knudsen et al. | |
| 2004/0180824 A1 | 9/2004 | Knudsen | |

FOREIGN PATENT DOCUMENTS

| | | |
|---|---|---|
| EP | 0708179 | 4/1998 |
| EP | 1512410 | 3/2005 |
| WO | WO 91/11457 | 8/1991 |
| WO | WO 98/05351 | 2/1998 |
| WO | WO 98/08531 | 3/1998 |
| WO | WO 98/30231 | 7/1998 |
| WO | WO 99/07404 | 2/1999 |
| WO | WO 99/25727 | 5/1999 |
| WO | WO 99/25728 | 5/1999 |
| WO | WO 99/40788 | 8/1999 |
| WO | WO 00/66138 | 11/2000 |
| WO | WO 01/27128 | 4/2001 |
| WO | WO 01/87322 | 11/2001 |
| WO | WO 01/89554 | * 11/2001 |
| WO | WO 01/98331 | 11/2001 |
| WO | WO 01/98324 | 12/2001 |
| WO | WO 02/40448 | 5/2002 |
| WO | WO 02/48192 | 6/2002 |
| WO | WO 02/083066 | 10/2002 |
| WO | WO 02/085406 | 10/2002 |
| WO | WO 03/059372 | 7/2003 |
| WO | WO 03/061362 | 7/2003 |
| WO | WO 03/084563 | 10/2003 |

OTHER PUBLICATIONS

Adelhorst et al., J. Biol. Chem. 269(9):6275-6278 (1994): *Structure-Activity Studies of Glucagon-Like Peptide-1*.
Bartlett et al., Bioorganic Chem 14:356-377 (1986): *Inhibition of Chymotrypsin by Phosphonate and Phosphonamidate Peptide Analogs*.
Bork et al., Trends in Genetics 12(10:425-427 (1996): *Go hunting in sequence databases but watch out for the traps*.
Bork, Genome Res 10:398-400 (2000): *Powers and pitfalls in sequence analysis: The 70% hurdle*.
Byrne et al., Diabet. Med. 13(10):854-860 (1996) (Abstract): *Human Studies with Glucagon-Like-Peptide-1: Potential of the gut Hormone for Clinical Use*.
D'Alessio et al., J. Clin. Invest. 97(1):133-138 (1996): *Elimination of the Action of Glucagon-Like Peptide 1 Causes and Impairment of Glucose Tolerance after Nutrient Ingestion by Healthy Baboons*.
Deacon et al., Diabetologia 40(Suppl 1):A127, Abstract No. 492 (1997): *Dipeptidyl Peptidase IV Resistant Analogues of Glucagon-Like Peptidek-1: In Vitro and In Vivo Studies*.
Doerks et al., Trends in Genetics 14(6):248-250 (1998): *Protein annotation: Detective work for function prediction*.

(Continued)

*Primary Examiner* — Elly-Gerald Stoica
(74) *Attorney, Agent, or Firm* — Womble Carlyle Sandridge & Rice LLP

(57) ABSTRACT

Compositions of the invention, including compounds that bind to a receptor for a glucagon-like peptide-1, an incretin, a glucagon-like peptide-1 (GLP-1), an exendin, or an agonist, an analog (preferably an agonist analog), a derivative, or a variant of any of aforementioned compounds, are used in the prevention and treatment of arrhythmias associated with cardiac ischemia, cardiac ischemia-perfusion and/or congestive heart failure. The invention relates to both the method and compositions for such treatment.

17 Claims, No Drawings

OTHER PUBLICATIONS

Eng et al., J. Biol. Chem. 265(33):20259-20262 (1990): *Purification and Structure of Exendin-3, a New Pancreatic Secretagogue Isolated from Heloderma horridum Venom.*

Eng et al., J. Biol. Chem. 267(11):7402-7405 (1992): *Isolation and Characterization of Exendin-4, and exendin-3 Analogue, from Heloderma suspectum Venom.*

Hareter et al., Diabetes 46(Suppl. 1):191A, Abstract No. 0734 (1997): *Role of Histidine 7 in GLP-1(7-36)amide Action.*

Hjorth et al., J. Biol. Chem. 269(48):30121-30124 (1994): *Glucagon and Glucagon-Like Peptide 1: Selective Receptor Recognition via Distinct Peptide Epitopes.*

Holz et al., Comp. Biochem. Biophysiol. 121(2):177-184 (Abstract) (1998): *Black Widow Spider Alpha-Latrotoxin: A Presynaptic Neurotoxin thatShares Structural Homology with the Glucagon-Like Peptide-1 Family of Insulin Secretagogic Hormones.*

Irwin et al., Proc. Natl. Acad. Sci USA 94:7915-7920 (1997): *The Xenopus Proglucagon Gene Encodes Novel GLP-1-Like-Peptides with Insulinotropic Properties.*

Mojsov, Int. J. Pepti. Protein Res. 40(3-4):333-343 (Abstract) (1992): *Structural Requirements for Biological Activity of Glucagon-Like Peptide-1.*

Ngo et al., *The Protein Folding Problem and Tertiary Structure Prediction*, pp. 492-495 (1994): *Computational complexity, protein structure prediction, and the Levinthal Paradox.*

Nikolaidis et al., J. Am. Coll. Cardiol. 37(2)(Suppl. 1), Abstract #886-5, p. 218A (2001): *GLP-1 improves myocardial performance in conscious dogs with pacing induced heart failure.*

O'Halloran et al., J. Endocrinol. 126(1):169-173 (Abstract) (1990): *Glucagon-Like Peptide-1 (7-36)-N2: A Physiological Inhibitor of Gastric Acid Secretion in Man.*

Orskov et al., Diabetes 42(5):658-661 (Abstract) (1993): *Biological Effects and Metabolic Rates of glucagon-like Peptide-1 7-36 Amide and glucagonlike Peptide-1 7-37 in Healthy Subjects are Indistinguishable.*

Orskov et al., J. Clin. Invest. 87:415-423 (1991): *Proglucagon Products in Plasma of Noninsulin-dependent Diabetics and Nondiabetic Controls in the Fasting State and After Oral Glucose and Intravenous Arginine.*

Parkes et al., Metabolism 50:583-589 (2001): *Insulinotropic actions of Exendin-4 and glucagon-like peptide-1 in vivo and in vitro.*

Raufman et al., J. Biol. Chem. 267(30):21432-21437 (1992): *Truncated Glucagon-Like Peptide-1 Interacts with Exendin Receptors on Dispersed Acini from Guinea Pig Pancreas.*

Ritzel et al., J. Endocrinol. 159:93-102 (1998): *A Synthetic Glucagon-Like Peptide-1 Analog with Improved Plasma Stability.*

Schjoldager et al., Dig. Dis. Sci. 34(5):703-708 (Abstract) (1989): *GLP-1 (Glucagon-Like Peptide 1) and Truncated GLP-1, Fragments of Human Proglucagon, Inhibit Gastric Acid Secretion in Humans.*

Siegel et al., Diabetes 46(Suppl. 1):187A, Abstract No. 0719 (1997): *Biological Activity of GLP-1 analogues with N-Terminal Modification.*

Skolnick et al., Trends in Biotech 18(1):34-39 (2000): *From genes to protein structure and function: novel applications of computational approaches in the genomic era.*

Smith et al., Nature Biotech 15:1222-1223 (1997): *The challenges of genome sequence annotation or the devil is in the details.*

Waterman, Bulletin of Mathematical Biol. 46(4):473-500 (1984): *General Methods of Sequence Comparison.*

Wells, Biochem 29(37):8509-8517 (1990): *Additivity of mutational effects in proteins.*

Wettergren et al., Dig. Dis. Sci. 38(4):665-673 (Abstract) (1993): *Truncated GLP-1 (Proglucagon 78-107 amide) Inhibits Gastric and Pancreatic Functions in Man.*

Willms et al., J. Clin. Endocrinol. Metab. 81(1):327-332 (1996): *Gastric Emptying, Glucose Responses, and Insulin Secretion after a Liquid Test Meal: Effects of Exogenous Glucagon-Like Peptidd-1 (GLP-1-(7-36) Amide in Type 2 (Noninsulin-Dependent) Diabetic Patients.*

Yu et al., J. Hypertension 21:1125-1135 (2003): *Antihypertensive Effect of Glucagon-Like Peptide-1 in Dahl Salt-Sensitive Rats.*

\* cited by examiner

```
                        SEQUENCE LISTING

<160> NUMBER OF SEQ ID NOS: 49

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 1

His Ala Glu Gly Thr Phe Thr Ser Asp Val Ser Ser Tyr Leu Glu Gly
 1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)
<223> OTHER INFORMATION: Lys or Arg
<220> FEATURE:
<221> NAME/KEY: MOD_RES
<222> LOCATION: (30)
<223> OTHER INFORMATION: Gly or not present
<220> FEATURE:
<223> OTHER INFORMATION: May be c-term amidated

<400> SEQUENCE: 2

Ala Glu Gly Thr Phe Thr Ser Asp Val Ser Ser Tyr Leu Glu Gly Gln
 1               5                   10                  15

Ala Ala Xaa Glu Phe Ile Ala Trp Leu Val Lys Gly Arg Xaa
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ser, Val, Asp, Thr, Phe, Gly, Glu, Ala, or not
      present
<220> FEATURE:
<221> NAME/KEY: MOD_RES
<222> LOCATION: (2)
<223> OTHER INFORMATION: Ser Val, Asp, Thr, Phe, Gly, Glu, or not
      present
<220> FEATURE:
<221> NAME/KEY: MOD_RES
<222> LOCATION: (3)
<223> OTHER INFORMATION: Ser, Val Asp, Thr, Phe, Gly, or not present
<220> FEATURE:
```

```
<221> NAME/KEY: MOD_RES
<222> LOCATION: (4)
<223> OTHER INFORMATION: Ser, Val, Asp, Thr, Phe, or not present
<220> FEATURE:
<221> NAME/KEY: MOD_RES
<222> LOCATION: (5)
<223> OTHER INFORMATION: Ser, Val, Asp, Thr, Phe, or not present
<220> FEATURE:
<221> NAME/KEY: MOD_RES
<222> LOCATION: (6)
<223> OTHER INFORMATION: Ser, Val, Asp, Thr, or not present
<220> FEATURE:
<221> NAME/KEY: MOD_RES
<222> LOCATION: (7)
<223> OTHER INFORMATION: Ser, Val, Asp, or not present
<220> FEATURE:
<221> NAME/KEY: MOD_RES
<222> LOCATION: (8)
<223> OTHER INFORMATION: Ser, Val, Asp, or not present
<220> FEATURE:
<221> NAME/KEY: MOD_RES
<222> LOCATION: (9)
<223> OTHER INFORMATION: Ser, Val, or not present
<220> FEATURE:
<221> NAME/KEY: MOD_RES
<222> LOCATION: (10)
<223> OTHER INFORMATION: Ser or not present
<220> FEATURE:
<221> NAME/KEY: MOD_RES
<222> LOCATION: (27)
<223> OTHER INFORMATION: Lys or Arg
<220> FEATURE:
<221> NAME/KEY: MOD_RES
<222> LOCATION: (30)
<223> OTHER INFORMATION: Gly or not present
<220> FEATURE:
<223> OTHER INFORMATION: May be c-term amidated

<400> SEQUENCE: 3

Xaa Xaa Xaa Xaa Xaa Xaa Xaa Xaa Xaa Xaa Ser Tyr Leu Glu Gly Gln
 1               5                  10                  15

Ala Ala Lys Glu Phe Ile Ala Trp Leu Val Xaa Gly Arg Xaa
            20                  25                  30

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Asp Val Ser
 1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ser Asp Val Ser
 1               5

<210> SEQ ID NO 6
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 6

Phe Thr Ser Asp Val Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Thr Ser Asp Val Ser
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Thr Phe Thr Ser Asp Val Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Gly Thr Phe Thr Ser Asp Val Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Glu Gly Thr Phe Thr Ser Asp Val Ser
1               5                   10

<210> SEQ ID NO 11
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Arg or not present
```

```
<220> FEATURE:
<221> NAME/KEY: MOD_RES
<222> LOCATION: (31)
<223> OTHER INFORMATION: Gly or not present

<400> SEQUENCE: 11

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Xaa Xaa Xaa
             20                  25                  30

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 12

His Ser Asp Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 13

Asp Leu Ser Lys Gln Met Glu Glu Glu Ala Val Arg Leu Phe Ile Glu
  1               5                  10                  15

Trp Leu Lys Asn Gly Gly Pro Ser Ser Gly Ala Pro Pro Pro Ser
             20                  25                  30

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 14

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 15
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 17

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 18
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 18

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35
```

```
<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 20

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 21

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 22

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 23
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 23

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 24
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 24

His Gly Glu Gly Thr Phe Thr Ser Asp Leu Ser Lys Gln Leu Glu Glu
  1               5                  10                  15

Glu Ala Val Arg Leu Ala Ile Glu Phe Leu Lys Asn
             20                  25

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
```

```
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Ala, Phe, Tyr, or naphthylalanine
<220> FEATURE:
<221> NAME/KEY: MOD_RES
<222> LOCATION: (23)
<223> OTHER INFORMATION: Ile, Val, Leu, pentylglycine, tert-butylglycine,
      or Met
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, Phe, Tyr, or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, 3Hyp, 4Hyp, thioproline,
```

```
        N-alkylglycine, N-alkylpentylglycine,
        N-alkylalanine, or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, 3Hyp, 4Hyp, thioproline,
        N-alkylglycine, N-alkylpentylglycine,
        N-alkylalanine, or not present
<220> FEATURE:
<221> NAME/KEY: MOD_RES
<222> LOCATION: (37)
<223> OTHER INFORMATION: Pro, homoproline, 3Hyp, 4Hyp, thioproline,
        N-alkylglycine, N-alkylpentylglycine,
        N-alkylalanine, or not present
<220> FEATURE:
<221> NAME/KEY: MOD_RES
<222> LOCATION: (38)
<223> OTHER INFORMATION: Pro, homoproline, 3Hyp, 4Hyp, thioproline,
        N-alkylglycine, N-alkylpentylglycine,
        N-alkylalanine, or not present
<220> FEATURE:
<223> OTHER INFORMATION: May be c-term amidated

<400> SEQUENCE: 25

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)
<223> OTHER INFORMATION: His, Arg, Tyr, Ala, Norval, Val, or Norleu
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (4)
<223> OTHER INFORMATION: Ala, Norval, Val, Norleu, or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
```

-continued

```
<222> LOCATION: (6)
<223> OTHER INFORMATION: Phe, Tyr, or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Ala, Norval, Val, Norleu, Asp, or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr, or naphthylalanine
<220> FEATURE:
<221> NAME/KEY: MOD_RES
<222> LOCATION: (23)
<223> OTHER INFORMATION: Ile, Val, Leu, pentylglycine, tert-
      butylglycine, or Met
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, Phe, Tyr, or naphthylalanine
<220> FEATURE:
<221> NAME/KEY: MOD_RES
<222> LOCATION: (26)
<223> OTHER INFORMATION: Ala or Leu
<220> FEATURE:
```

```
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (37)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (39)
<223> OTHER INFORMATION: Ser or Tyr, preferably Ser
<220> FEATURE:
<223> OTHER INFORMATION: May be c-term amidated

<400> SEQUENCE: 26

Xaa Xaa Xaa Xaa Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)
<223> OTHER INFORMATION: His or Arg
<220> FEATURE:
<221> NAME/KEY: MOD_RES
<222> LOCATION: (2)
<223> OTHER INFORMATION: Gly or Ala
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, or pentylglycine
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, or pentylglycine
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
```

```
<223> OTHER INFORMATION: Phe or naphthylalanine
<220> FEATURE:
<221> NAME/KEY: MOD_RES
<222> LOCATION: (23)
<223> OTHER INFORMATION: Ile, Val, or tert-butylglycine
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, or Phe
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, thioproline,
      N-methylylalanine or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, thioproline,
      N-methylylalanine or not present
<220> FEATURE:
<221> NAME/KEY: MOD_RES
<222> LOCATION: (37)
<223> OTHER INFORMATION: Pro, homoproline, thioproline,
      N-methylylalanine or not present
<220> FEATURE:
<221> NAME/KEY: MOD_RES
<222> LOCATION: (38)
<223> OTHER INFORMATION: Pro, homoproline, thioproline,
      N-methylylalanine or not present
<220> FEATURE:
<223> OTHER INFORMATION: May be c-term amidated

<400> SEQUENCE: 27

Xaa Xaa Xaa Gly Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa Xaa
            20                  25                  30
```

Xaa Xaa Xaa Xaa Xaa Xaa
         35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His or Ala
<220> FEATURE:
<221> NAME/KEY: MOD_RES
<222> LOCATION: (2)
<223> OTHER INFORMATION: Gly or Ala
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (4)
<223> OTHER INFORMATION: Ala or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Phe or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Ala, Asp, or Glu
<220> FEATURE:
<221> NAME/KEY: MOD_RES
<222> LOCATION: (10)
<223> OTHER INFORMATION: Ala, Leu, or pentylglycine
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Met, or pentylglycine
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:

```
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe or naphthylalanine
<220> FEATURE:
<221> NAME/KEY: MOD_RES
<222> LOCATION: (23)
<223> OTHER INFORMATION: Ile, Val, or tert-butylglycine
<220> FEATURE:
<221> NAME/KEY: MOD_RES
<222> LOCATION: (24)
<223> OTHER INFORMATION: Ala, Glu, or Asp
<220> FEATURE:
<221> NAME/KEY: MOD_RES
<222> LOCATION: (25)
<223> OTHER INFORMATION: Ala, Trp, or Phe
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)
<223> OTHER INFORMATION: Gly or not present
<220> FEATURE:
<221> NAME/KEY: MOD_RES
<222> LOCATION: (30)
<223> OTHER INFORMATION: Gly or not present
<220> FEATURE:
<221> NAME/KEY: MOD_RES
<222> LOCATION: (31)
<223> OTHER INFORMATION: Pro, homoproline, thioproline,
     N-methylylalanine or not present
<220> FEATURE:
<221> NAME/KEY: MOD_RES
<222> LOCATION: (32)
<223> OTHER INFORMATION: Ser or not present
<220> FEATURE:
<221> NAME/KEY: MOD_RES
<222> LOCATION: (33)
<223> OTHER INFORMATION: Ser or not present
<220> FEATURE:
<221> NAME/KEY: MOD_RES
<222> LOCATION: (34)
<223> OTHER INFORMATION: Gly or not present
<220> FEATURE:
<221> NAME/KEY: MOD_RES
<222> LOCATION: (35)
<223> OTHER INFORMATION: Ala or not present
<220> FEATURE:
<221> NAME/KEY: MOD_RES
<222> LOCATION: (36)
<223> OTHER INFORMATION: Pro, homoproline, thioproline,
     N-methylylalanine or not present
<220> FEATURE:
<221> NAME/KEY: MOD_RES
<222> LOCATION: (37)
<223> OTHER INFORMATION: Pro, homoproline, thioproline,
     N-methylylalanine or not present
<220> FEATURE:
<221> NAME/KEY: MOD_RES
```

```
<222> LOCATION: (38)
<223> OTHER INFORMATION: Pro, homoproline, thioproline,
      N-methylylalanine or not present
<220> FEATURE:
<221> NAME/KEY: MOD_RES
<222> LOCATION: (39)
<223> OTHER INFORMATION: Ser or not present
<220> FEATURE:
<223> OTHER INFORMATION: May be c-term amidated

<400> SEQUENCE: 28

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 29
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, or Tyr
<220> FEATURE:
<221> NAME/KEY: MOD_RES
<222> LOCATION: (2)
<223> OTHER INFORMATION: Ser, Gly, Ala, or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr, or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
```

```
<223> OTHER INFORMATION: Ala, Leu, Ile, pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala, Leu, or Lys-NH
<220> FEATURE:
<221> NAME/KEY: MOD_RES
<222> LOCATION: (22)
<223> OTHER INFORMATION: Lys, Arg, or not present
<220> FEATURE:
<221> NAME/KEY: MOD_RES
<222> LOCATION: (23)
<223> OTHER INFORMATION: Phe, Tyr, or naphthylalanine
<220> FEATURE:
<221> NAME/KEY: MOD_RES
<222> LOCATION: (24)
<223> OTHER INFORMATION: Ile, Val, Leu, pentylglycine, tert-
      butylglycine, or Met
<220> FEATURE:
<221> NAME/KEY: MOD_RES
<222> LOCATION: (25)
<223> OTHER INFORMATION: Ala, Glu, or Asp
<220> FEATURE:
<221> NAME/KEY: MOD_RES
<222> LOCATION: (26)
<223> OTHER INFORMATION: Ala, Trp, Phe, Tyr, or naphthylalanine
<220> FEATURE:
<221> NAME/KEY: MOD_RES
<222> LOCATION: (27)
<223> OTHER INFORMATION: Ala or Leu
<220> FEATURE:
<221> NAME/KEY: MOD_RES
<222> LOCATION: (28)
<223> OTHER INFORMATION: Lys, Asn, Lys-NH, or Ala
<220> FEATURE:
<221> NAME/KEY: MOD_RES
<222> LOCATION: (29)
<223> OTHER INFORMATION: Asn, Lys, Arg, or Lys-NH
<220> FEATURE:
<221> NAME/KEY: MOD_RES
<222> LOCATION: (30)
<223> OTHER INFORMATION: Asn, Lys, Arg, Ala, or not present
<220> FEATURE:
<221> NAME/KEY: MOD_RES
<222> LOCATION: (31)
<223> OTHER INFORMATION: Gly or not present
<220> FEATURE:
<221> NAME/KEY: MOD_RES
<222> LOCATION: (32)
<223> OTHER INFORMATION: Gly or not present
<220> FEATURE:
<221> NAME/KEY: MOD_RES
<222> LOCATION: (33)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (34)
<223> OTHER INFORMATION: Ser or not present
```

-continued

```
<220> FEATURE:
<221> NAME/KEY: MOD_RES
<222> LOCATION: (35)
<223> OTHER INFORMATION: Ser or not present
<220> FEATURE:
<221> NAME/KEY: MOD_RES
<222> LOCATION: (36)
<223> OTHER INFORMATION: Gly or not present
<220> FEATURE:
<221> NAME/KEY: MOD_RES
<222> LOCATION: (37)
<223> OTHER INFORMATION: Ala or not present
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (39)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (40)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<223> OTHER INFORMATION: May be c-term amidated

<400> SEQUENCE: 29

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa
         35                  40

<210> SEQ ID NO 30
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, Tyr, Ala, Norval, Val, or Norleu
<220> FEATURE:
<221> NAME/KEY: MOD_RES
<222> LOCATION: (2)
<223> OTHER INFORMATION: Ser, Gly, Ala, or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (4)
<223> OTHER INFORMATION: Ala, Norval, Val, Norleu, or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Phe, Tyr, or naphthylalanine
<220> FEATURE:
<221> NAME/KEY: MOD_RES
<222> LOCATION: (7)
<223> OTHER INFORMATION: Thr or Ser
```

```
<220> FEATURE:
<221> NAME/KEY: MOD_RES
<222> LOCATION: (8)
<223> OTHER INFORMATION: Ala, Ser, or Thr
<220> FEATURE:
<221> NAME/KEY: MOD_RES
<222> LOCATION: (9)
<223> OTHER INFORMATION: Ala, Norval, Val, Norleu, Asp, or Glu
<220> FEATURE:
<221> NAME/KEY: MOD_RES
<222> LOCATION: (10)
<223> OTHER INFORMATION: Ala, Leu, ile, Val, pentylglycine, or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val, or Met
<220> FEATURE:
<221> NAME/KEY: MOD_RES
<222> LOCATION: (15)
<223> OTHER INFORMATION: Ala or Glu
<220> FEATURE:
<221> NAME/KEY: MOD_RES
<222> LOCATION: (16)
<223> OTHER INFORMATION: Ala or Glu
<220> FEATURE:
<221> NAME/KEY: MOD_RES
<222> LOCATION: (17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala, Leu, or Lys-NH
<220> FEATURE:
<221> NAME/KEY: MOD_RES
<222> LOCATION: (22)
<223> OTHER INFORMATION: Lys, Arg, or not present
<220> FEATURE:
<221> NAME/KEY: MOD_RES
<222> LOCATION: (23)
<223> OTHER INFORMATION: Phe, Tyr, or naphthylalanine
<220> FEATURE:
<221> NAME/KEY: MOD_RES
<222> LOCATION: (24)
<223> OTHER INFORMATION: Ile, Val, Leu, pentylglycine, tert-
      butylglycine, or Met
<220> FEATURE:
<221> NAME/KEY: MOD_RES
<222> LOCATION: (25)
<223> OTHER INFORMATION: Ala, Glu, or Asp
<220> FEATURE:
<221> NAME/KEY: MOD_RES
<222> LOCATION: (26)
<223> OTHER INFORMATION: Ala, Trp, Phe, Tyr, or naphthylalanine
<220> FEATURE:
<221> NAME/KEY: MOD_RES
<222> LOCATION: (27)
<223> OTHER INFORMATION: Ala or Leu
<220> FEATURE:
<221> NAME/KEY: MOD_RES
<222> LOCATION: (28)
```

```
<223> OTHER INFORMATION: Lys, Asn, Lys-NH, or Ala
<220> FEATURE:
<221> NAME/KEY: MOD_RES
<222> LOCATION: (29)
<223> OTHER INFORMATION: Asn, Lys, Arg, or Lys-NH
<220> FEATURE:
<221> NAME/KEY: MOD_RES
<222> LOCATION: (30)
<223> OTHER INFORMATION: Asn, Lys, Arg, Ala, or not present
<220> FEATURE:
<221> NAME/KEY: MOD_RES
<222> LOCATION: (31)
<223> OTHER INFORMATION: Gly or not present
<220> FEATURE:
<221> NAME/KEY: MOD_RES
<222> LOCATION: (32)
<223> OTHER INFORMATION: Gly or not present
<220> FEATURE:
<221> NAME/KEY: MOD_RES
<222> LOCATION: (33)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (34)
<223> OTHER INFORMATION: Ser or not present
<220> FEATURE:
<221> NAME/KEY: MOD_RES
<222> LOCATION: (35)
<223> OTHER INFORMATION: Ser or not present
<220> FEATURE:
<221> NAME/KEY: MOD_RES
<222> LOCATION: (36)
<223> OTHER INFORMATION: Gly or not present
<220> FEATURE:
<221> NAME/KEY: MOD_RES
<222> LOCATION: (37)
<223> OTHER INFORMATION: Ala or not present
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (39)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (40)
<223> OTHER INFORMATION: Pro, homoproline, 3Hyp, 4Hyp, thioproline,
      N-alkylglycine, N-alkylpentylglycine,
      N-alkylalanine, or not present
<220> FEATURE:
<221> NAME/KEY: MOD_RES
<222> LOCATION: (41)
<223> OTHER INFORMATION: Ser or Tyr, preferably Ser
<220> FEATURE:
<223> OTHER INFORMATION: May be c-term amidated

<400> SEQUENCE: 30

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa
         35                  40

<210> SEQ ID NO 31
<211> LENGTH: 39
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, or Tyr
<220> FEATURE:
<221> NAME/KEY: MOD_RES
<222> LOCATION: (2)
<223> OTHER INFORMATION: Ser, Gly, Ala, or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (6)
<223> OTHER INFORMATION: Phe, Tyr, or naphthalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine, or Met
<220> FEATURE:
<221> NAME/KEY: MOD_RES
<222> LOCATION: (14)
<223> OTHER INFORMATION: Leu, Ile, pentylglycine, Val, or Met
<220> FEATURE:
<221> NAME/KEY: MOD_RES
<222> LOCATION: (22)
<223> OTHER INFORMATION: Phe, Tyr, or naphthalanine
<220> FEATURE:
<221> NAME/KEY: MOD_RES
<222> LOCATION: (23)
<223> OTHER INFORMATION: Ile, Val, Leu, pentylglycine, tert-
      butylglycine, or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr, or naphthylalanine
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (36)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (37)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine, or
      N-alkylalanine
```

```
<220> FEATURE:
<221> NAME/KEY: MOD_RES
<222> LOCATION: (39)
<223> OTHER INFORMATION: Ser, Thr, or Tyr
<220> FEATURE:
<223> OTHER INFORMATION: May be c-term amidated

<400> SEQUENCE: 31

Xaa Xaa Xaa Gly Thr Xaa Xaa Xaa Xaa Xaa Ser Lys Gln Xaa Glu Glu
 1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 32
<211> LENGTH: 40
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, or Tyr
<220> FEATURE:
<221> NAME/KEY: MOD_RES
<222> LOCATION: (2)
<223> OTHER INFORMATION: Ser, Gly, Ala, or Thr
<220> FEATURE:
<221> NAME/KEY: MOD_RES
<222> LOCATION: (3)
<223> OTHER INFORMATION: Ala, Asp, or Glu
<220> FEATURE:
<221> NAME/KEY: MOD_RES
<222> LOCATION: (6)
<223> OTHER INFORMATION: Phe, Tyr, or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine, or Met
<220> FEATURE:
<221> NAME/KEY: MOD_RES
<222> LOCATION: (14)
<223> OTHER INFORMATION: Leu, Ile, pentylglycine, Val, or Met
<220> FEATURE:
<221> NAME/KEY: MOD_RES
<222> LOCATION: (22)
<223> OTHER INFORMATION: Phe, Tyr, or naphthylalanine
<220> FEATURE:
<221> NAME/KEY: MOD_RES
<222> LOCATION: (23)
<223> OTHER INFORMATION: Ile, Val, Leu, pentylglycine, tert-
      butylglycine, or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr, or naphthylalanine
<220> FEATURE:
```

```
<221> NAME/KEY: MOD_RES
<222> LOCATION: (27)
<223> OTHER INFORMATION: Lys, Asn, or Lys-NH
<220> FEATURE:
<221> NAME/KEY: MOD_RES
<222> LOCATION: (28)
<223> OTHER INFORMATION: Asn, Lys, Arg, or Lys-NH
<220> FEATURE:
<221> NAME/KEY: MOD_RES
<222> LOCATION: (29)
<223> OTHER INFORMATION: Asn, Lys, Arg, or not present
<220> FEATURE:
<221> NAME/KEY: MOD_RES
<222> LOCATION: (32)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (37)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (38)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (39)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (40)
<223> OTHER INFORMATION: Ser, Thr, or Tyr
<220> FEATURE:
<223> OTHER INFORMATION: May be c-term amidated

<400> SEQUENCE: 32

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Xaa Xaa Xaa Gly Gly Xaa
            20                  25                  30

Ser Ser Gly Ala Xaa Xaa Xaa Xaa
        35                  40

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, D-His, desamino-His, 2-amino-His,
      beta-hydroxy-His, homohistidine,
      alpha-fluoromethyl-His, or alpha-methyl-His
<220> FEATURE:
<221> NAME/KEY: MOD_RES
<222> LOCATION: (2)
<223> OTHER INFORMATION: Met, Asp, Lys, Thr, Leu, Asn, Gln, Phe, Val, or
      Tyr
<220> FEATURE:
<221> NAME/KEY: MOD_RES
<222> LOCATION: (15)
<223> OTHER INFORMATION: Glu, Gln, Ala, Thr, Ser, or Gly
<220> FEATURE:
<221> NAME/KEY: MOD_RES
<222> LOCATION: (21)
<223> OTHER INFORMATION: Glu, Gln, Ala, Thr, Ser, or Gly
```

```
<220> FEATURE:
<221> NAME/KEY: MOD_RES
<222> LOCATION: (31)
<223> OTHER INFORMATION: Gly or not present
<220> FEATURE:
<223> OTHER INFORMATION: May be c-term amidated

<400> SEQUENCE: 33

Xaa Xaa Glu Gly Thr Phe Thr Ser Asp Val Ser Ser Tyr Leu Xaa Gly
 1               5                  10                  15

Gln Ala Ala Lys Xaa Phe Ile Ala Trp Leu Val Lys Gly Arg Xaa
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, D-His, desamino-His, 2-amino-His,
      beta-hydroxy-His, homohistidine,
      alpha-fluoromethyl-His, or alpha-methyl-His
<220> FEATURE:
<221> NAME/KEY: MOD_RES
<222> LOCATION: (2)
<223> OTHER INFORMATION: Ala, Gly, Val, Thr, Ile, or alpha-methyl-Ala
<220> FEATURE:
<221> NAME/KEY: MOD_RES
<222> LOCATION: (15)
<223> OTHER INFORMATION: Glu, Gln, Ala, Thr, Ser, or Gly
<220> FEATURE:
<221> NAME/KEY: MOD_RES
<222> LOCATION: (21)
<223> OTHER INFORMATION: Glu, Gln, Ala, Thr, Ser, or Gly
<220> FEATURE:
<221> NAME/KEY: MOD_RES
<222> LOCATION: (31)
<223> OTHER INFORMATION: Gly or not present
<220> FEATURE:
<223> OTHER INFORMATION: May be c-term amidated

<400> SEQUENCE: 34

Xaa Xaa Glu Gly Thr Phe Thr Ser Asp Val Ser Ser Tyr Leu Xaa Gly
 1               5                  10                  15

Gln Ala Ala Lys Xaa Phe Ile Ala Trp Leu Val Lys Gly Arg Xaa
            20                  25                  30

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 35

Gly Gly Xaa Ser Ser
 1               5

<210> SEQ ID NO 36
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 36

Gly Gly Xaa Ser Ser Gly
 1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 37

Gly Gly Xaa Ser Ser Gly Ala
 1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 38

Gly Gly Xaa Ser Ser Gly Ala Xaa
 1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (9)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 39

Gly Gly Xaa Ser Ser Gly Ala Xaa Xaa
 1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (9)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (10)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<223> OTHER INFORMATION: May be c-term amidated

<400> SEQUENCE: 40

Gly Gly Xaa Ser Ser Gly Ala Xaa Xaa Xaa
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
```

```
<222> LOCATION: (8)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (9)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (10)
<223> OTHER INFORMATION: Pro, homoproline, 3Hyp, 4Hyp, thioproline,
      N-alkylglycine, N-alkylpentylglycine, or
      N-alkylalanine
<220> FEATURE:
<221> NAME/KEY: MOD_RES
<222> LOCATION: (11)
<223> OTHER INFORMATION: Ser or Tyr, preferably Ser
<220> FEATURE:
<223> OTHER INFORMATION: May be c-term amidated

<400> SEQUENCE: 41

Gly Gly Xaa Ser Ser Gly Ala Xaa Xaa Xaa Xaa
  1               5                  10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 42

Gly Gly Xaa Ser Ser
  1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 43

Gly Gly Xaa Ser Ser Gly
  1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 44

Gly Gly Xaa Ser Ser Gly Ala
 1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<221> NAME/KEY: MOD_RES
<222> LOCATION: (8)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 45

Gly Gly Xaa Ser Ser Gly Ala Xaa
 1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<221> NAME/KEY: MOD_RES
<222> LOCATION: (8)
<223> OTHER INFORMATION: Pro, homoproline, thioproline,
      N-methylylalanine, or not present
<220> FEATURE:
<221> NAME/KEY: MOD_RES
<222> LOCATION: (9)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 46

Gly Gly Xaa Ser Ser Gly Ala Xaa Xaa
 1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
```

```
              N-methylylalanine, or not present
<220> FEATURE:
<221> NAME/KEY: MOD_RES
<222> LOCATION: (8)
<223> OTHER INFORMATION: Pro, homoproline, thioproline,
      N-methylylalanine, or not present
<220> FEATURE:
<221> NAME/KEY: MOD_RES
<222> LOCATION: (9)
<223> OTHER INFORMATION: Pro, homoproline, thioproline,
      N-methylylalanine, or not present
<220> FEATURE:
<221> NAME/KEY: MOD_RES
<222> LOCATION: (10)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 47

Gly Gly Xaa Ser Ser Gly Ala Xaa Xaa Xaa
  1               5                  10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<221> NAME/KEY: MOD_RES
<222> LOCATION: (8)
<223> OTHER INFORMATION: Pro, homoproline, thioproline,
      N-methylylalanine, or not present
<220> FEATURE:
<221> NAME/KEY: MOD_RES
<222> LOCATION: (9)
<223> OTHER INFORMATION: Pro, homoproline, thioproline,
      N-methylylalanine, or not present
<220> FEATURE:
<221> NAME/KEY: MOD_RES
<222> LOCATION: (10)
<223> OTHER INFORMATION: Pro, homoproline, thioproline,
      N-methylylalanine, or not present
<220> FEATURE:
<223> OTHER INFORMATION: May be c-term amidated

<400> SEQUENCE: 48

Gly Gly Xaa Ser Ser Gly Ala Xaa Xaa Xaa Ser
  1               5                  10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline,
      N-methylylalanine, or not present
<220> FEATURE:
<221> NAME/KEY: MOD_RES
<222> LOCATION: (8)
<223> OTHER INFORMATION: Pro, homoproline, thioproline,
      N-methylylalanine, or not present
<220> FEATURE:
<221> NAME/KEY: MOD_RES
```

-continued

```
<222> LOCATION: (9)
<223> OTHER INFORMATION: Pro, homoproline, thioproline,
      N-methylylalanine, or not present
<220> FEATURE:
<221> NAME/KEY: MOD_RES
<222> LOCATION: (10)
<223> OTHER INFORMATION: Pro, homoproline, thioproline,
      N-methylylalanine, or not present
<220> FEATURE:
<221> NAME/KEY: MOD_RES
<222> LOCATION: (11)
<223> OTHER INFORMATION: Ser or Tyr, preferably Ser
<220> FEATURE:
<223> OTHER INFORMATION: May be c-term amidated

<400> SEQUENCE: 49

Gly Gly Xaa Ser Ser Gly Ala Xaa Xaa Xaa Xaa
 1               5                   10
```

TREATMENT OF CARDIAC ARRHYTHMIAS

CROSS REFERENCE TO RELATED APPLICATIONS

This application is a divisional of U.S. application Ser. No. 10/740,146, filed Dec. 17, 2003, which claims the benefit of priority to U.S. Provisional Application No. 60/434,508, filed Dec. 17, 2002, and U.S. Provisional Application No. 60/434,888, filed Dec. 19, 2002, which are hereby incorporated by reference in their entireties.

INCORPORATION OF SEQUENCE LISTING

A paper copy of the Sequence listing, filed in the parent application U.S. Ser. No. 10/740,146 on Sep. 9, 2004, and a computer readable form of the sequence listing on diskette, containing the file named 18528.677.SeqList.txt, which is 46,836 bytes in size (measured in MS-DOS), recorded on and filed on Sep. 9, 2004, are hereby incorporated by reference.

FIELD OF THE INVENTION

This invention relates to compositions and methods for preventing cardiac arrhythmias using a compound that binds to a receptor for a glucagon-like peptide-1, an incretin, a glucagon-like peptide-1 (GLP-1), an exendin, or an agonist, an analog (preferably an agonist analog), a derivative, or a variant of any of aforementioned compounds and fragments thereof.

BACKGROUND OF THE INVENTION

Cardiac arrhythmias and ischemic heart disease afflict an estimated 20 million Americans, and possibly ten times as many people worldwide. If left undetected and untreated, they often result in heart attacks and deaths.

An arrhythmia is an irregular heartbeat. The heart beats on its own due to its natural pacemaker, a small cluster of specialized cells called the sinoatrial node (S-A node). The S-A node is located in the right atrium and produces electrical signals at regular intervals that are sent through a pathway in the heart muscle. The S-A node signals follow a natural electrical pathway that helps the heart beat efficiently. An electrical impulse travels from the S-A node through the atrioventricular node (A-V node), a second cluster of cells located near the center of the heart. The A-V node then sends the signals out to the walls of the ventricles.

Normally, the two ventricles contract a fraction of a second after they have been filled with blood from an atrial contraction. This timing sequence is called atrio-ventricular synchrony. Sometimes, however, something goes wrong with the heart's electrical system, and the heartbeat becomes arrhythmic. An arrhythmia can occur when: (1) the S-A node develops an abnormal rate or rhythm; (2) the normal electrical pathway is interrupted, or (3) another part of the heart tries to take over as the pacemaker. Though there are several types of arrhythmias, they all have the commonality of preventing the heart from pumping blood efficiently.

Fast, abnormal heart rhythms, usually over 100 beats per minute, are called tachyarrhythmias. When the heart's electrical signals come from the ventricle instead of the S-A node, this causes an arrhythmia known as ventricular tachycardia (VT). As the heart beats faster, it pumps less blood because there is not enough time for the heart to fill with blood between beats. If this fast heartbeat continues, the brain and body may not receive enough blood and oxygen, causing fainting spells, blackouts, temporary blind spots or dizziness. Eventually, the patient may become unconscious and in extreme cases the heart may stop (cardiac arrest). The most common cause of arrhythmias is heart disease, particularly coronary artery disease, abnormal heart valve function, and heart failure.

VT is a frequent precursor to another type of arrhythmia, ventricular fibrillation (VF). In VF, the heart beats much faster than normal, sometimes over 300 beats a minute. The ventricles "quiver" during VF and do not carry out coordinated contractions. Because little blood is pumped from the heart, VF is a form of cardiac arrest and is fatal unless treated immediately.

Arrhythmias complicate all forms of cardiac disease. Ventricular tachycardia and fibrillation occur commonly in the setting of ischemic heart disease and congestive heart failure (CHF). In the setting of myocardial infarction, ventricular arrhythmias may develop secondarily to ischemia or reperfusion. Reperfusion occurs subsequent to therapies that reestablish flow in an artery that is obstructed by a blood clot, i.e. thrombolytic agents or following an intervention, such as angioplasty, coronary bypass grafting or placement of an intracoronary stent.

A major problem in congestive heart failure is stress hyperglycemia and insulin resistance. As a result of the combination of high circulating levels of free fatty acids and reduced glucose uptake, there is a shift toward fatty acid oxidation, depletion of Krebs cycle intermediates and diminished glucose oxidation. These changes ultimately lead to reduced levels of CrP and loss of energy reserve.

Although the mechanisms underlying ventricular arrhythmias are complex and not fully understood, it has been established that glycolysis plays an important role as the source of ATP to maintain the electrochemical gradient across the cardiac cellular membrane. Potassium ($K^+$), calcium ($Ca^{2+}$), and sodium ($Na^+$) gradients are all modulated by ATP that arises from glycolysis. Moreover, inhibition of glycolysis is arrhythmogenic, while glucose-insulin-potassium (GIK) infusions in the setting of ischemia are anti-arrhythmic.

Conventional treatment for arrhythmias is aimed at decreasing pacemaker activity and modifying impaired conduction. These treatments usually involve the use of sodium channel blockers, calcium channel blockers and/or beta blockers in an effort to decrease the automaticity, conduction, and excitability of the heart or increase the refractory period of cardiac muscle. While drug treatments are often effective against arrhythmias, drugs frequently have side effects and require the patient to remember to take them on a daily basis. Mild to moderate side effects associated with these drugs include drowsiness, dizziness, nausea, bradycardia, and low blood pressure, while more severe side effects include torsades des pointes (a form of VT) and even sudden death. Further, these drugs can actually cause arrhythmias at increased dosages due to their toxic effects on cardiac conduction at these levels.

Artificial pacemakers are also frequently used in the treatment of arrhythmias. Pacemakers are electronic devices that act in place of the heart's own pacemaker and are programmed to imitate the normal conduction sequence of the heart. Usually they are implanted surgically beneath the skin of the chest and have wires running to the heart. There are several disadvantages associated with the use of pacemakers, including the need to replace the units every 8-10 years and their potential to be interfered with by certain types of equipment, such as magnetic resonance imaging machines (MRIs).

Therapy for arrhythmias can also include devices that deliver a shock to the heart to stop an abnormal rhythm and restore a normal one. Using an electric shock for this purpose is called cardioversion, electroversion, or defibrillation. Usually in this procedure, a large machine that delivers a shock (a defibrillator) is used by a team of doctors and nurses to stop a life-threatening arrhythmia. More recently, a defibrillator about the size of a pack of cards can be implanted surgically in the patient. These small devices, which automatically sense life-threatening arrhythmias and deliver a shock, are used in people who would otherwise die when their heart suddenly stops. Because these defibrillators do not prevent arrhythmias, the patient usually must also take drugs as well.

There is, therefore, a need in the art for a safe and effective composition for preventing and treating cardiac arrhythmias. It is a primary objective of this the present invention to fulfill this need.

SUMMARY OF THE INVENTION

The invention describes compositions and methods for reducing the risk of suffering from, preventing, or treating cardiac arrhythmias. Compositions of the invention include a compound that binds to a receptor for a glucagon-like peptide-1, an incretin, a glucagon-like peptide-1 (GLP-1), an exendin, or an agonist, an analog (preferably an agonist analog), a derivative, or a variant of any of them, as well as biologically fragments thereof.

The present inventors have recognized that compositions of the invention, including GLP-1 and exendins, have anti-arrhythmic effects in patients with cardiac ischemia, cardiac ischemia-reperfusion, and congestive heart failure. For example, GLP-1 has been found to reduce cardiac injury and enhance recovery in patients with these disorders. Incretins, including GLP-1, are glucose-dependent insulinotropic hormones. GLP-1 and exendin effectively enhance peripheral glucose uptake without inducing dangerous hypoglycemia. They also strongly suppress glucagon secretion, independent of its insulinotropic action, and thereby powerfully reduce plasma free fatty acid (FFA) levels substantially more than can be accomplished with insulin. High FFA levels have been implicated as a major toxic mechanism during myocardial ischemia.

Accordingly, it is a primary objective of the present invention to provide compositions and methods for preventing and treating cardiac arrhythmias.

It is a further objective of the present invention to provide compositions and methods for preventing and treating cardiac arrhythmias that are effective in patients having cardiac ischemia, cardiac ischemia-reperfusion, and congestive heart failure.

It is yet a further objective of the present invention to provide compositions and methods for preventing and treating cardiac arrhythmias that reliably reduce injury associated with reperfusion and ischemia, and enhance patient recovery.

It is a further objective of the present invention to provide compositions and methods for preventing and treating cardiac arrhythmias without the side effects and disadvantages of conventional therapies.

Moreover, the compounds of the invention may be administered by any conventional means, including subcutaneously, intravenously, orally, transmucosally, intraperitoneally, or other means known in the art. The compositions are particularly useful in treating arrhythmias resulting from ischemic heart disease and congestive heart failure.

Thus, in one aspect, the invention contemplates a method for preventing and treating arrhythmias comprising administering to an individual an effective amount of a composition which includes a compound which binds to a receptor for glucagon-like peptide-1, an incretin, a glucagon-like peptide-1 (GLP-1), an exendin, or an agonist, an analog (preferably an agonist analog), a derivative, or a variant of any of aforementioned compounds, and biologically active fragments thereof.

In one embodiment, methods of the invention include administering compositions of the invention at a dose from about 0.1 pmol/kg/min. up to about 10 pmol/kg/min. Other dose ranges may be from about 0.01 pmol/kg to 20 nmol/kg. Further contemplated are a single or multiple injection(s) in a dose from about 0.005 nmol/kg to 20 nmol/kg.

In another embodiment, methods of the invention include a concurrent administration with any one or more of a glucose, a potassium, a free radical scavenger or an anti-oxidant.

In yet other embodiments of the invention, the compositions of the invention are administered within four hours of an ischemic event and may be continued following the ischemic event. The composition may be administered concurrently or as soon as possible following therapies that reestablish flow in an artery that has been obstructed, such as angioplasty, coronary bypass grafting, and placement of an intracoronary stent.

The compositions of the invention may be administered to treat ventricular arrhythmias. The ventricular arrhythmia may be caused by a condition selected from the group consisting of cardiac ischemia, cardiac ischemia-reperfusion, and congestive heart failure.

In another general aspect, methods of the invention includemetabolic intervention with a composition that includes a compound which binds to a receptor for glucagon-like peptide-1, an incretin, a glucagon-like peptide-1 (GLP-1), an exendin, or an agonist, an analog (preferably an agonist analog), a derivative, or a variant of any of aforementioned compounds, and fragments thereof to prevent or treat cardiac arrhythmias, said method comprising administering to an individual in need of such treatment an effective amount of a composition which includes a compound which binds to a receptor for glucagon-like peptide-1, an incretin, a glucagon-like peptide-1 (GLP-1), an exendin, or an agonist, an analog (preferably an agonist analog), a derivative, or a variant of any of aforementioned compounds, and biologically active fragments thereof.

The method and means of accomplishing each of the above objectives as well as others will become apparent from the detailed description of the invention, which follows hereafter.

DETAILED DESCRIPTION

The present invention relates to the development of compositions for the prevention and treatment of cardiac arrhythmias using an incretin, a glucagon-like peptide-1 (GLP-1), an exendin, a compound that binds to a receptor for glucagon-like peptide-1, or an agonist, an analog (preferably an agonist analog), a derivative, or a variant of any of the aforementioned compounds and biologically active fragments thereof. One premise forming the basis of this discovery is that compounds of the invention, including GLP-1, are effective at maintaining the electrochemical gradient across cardiac cellular membranes, thereby reducing the likelihood of arrhythmias developing.

Cardiac arrhythmias can develop due to a variety of factors. For instance, arrhythmias may develop secondary to ischemia or reperfusion. Heart muscle is largely dependent on uninterrupted blood flow, which guarantees delivery of oxygen and substrates to cells while washing out harmful metabolic products. Ischemia, e.g. resulting from decrease or cessation of myocardial blood flow, leads to rapid changes in myocardial metabolism. The degree of these changes is highly dependent upon the severity of the ischemia. For anatomical and physiological reasons, contractile myocytes in endocardium are the most vulnerable cells. Ischemia is a dynamic process. With rapid reperfusion, full recovery of myocardial metabolism occurs; but continuation of ischemia leads to total tissue necrosis in a few hours. Reperfusion, although generally considered beneficial, can cause tissue injury by several mechanisms, including oxidative stress, and thus affect the final recovery of the contractibility.

Total cessation of myocardial blood flow leads to rapid perturbations in myocardial metabolism. In a few seconds, oxygen dissolved in cytoplasm or bound to myoglobin is consumed, seriously disturbing oxidative phosphorylation and mitochondrial ATP production. Levels of high energy phosphates, mainly creatine phosphate and ATP, are decreased, and the breakdown products of adenine nucleotides, such as inorganic phosphate and adenosine, accumulate.

Liberation of free fatty acids in lipolysis is stimulated in myocardial ischemia by increased circulating catecholamines, but fatty acid oxidation and tricarboxylic acid cycle are inhibited. This leads to cytosolic accumulation of free fatty acid CoA-esters and inhibition of adenine nucleotide translocase. Glycogenolysis and anaerobic glycolysis are stimulated, leading to accumulation of lactate and $H^+$-ions and intracellular acidosis. Finally, the accumulation of proteins, lactate, and reduced form of NADH leads to inhibition of glycolysis and anaerobic energy production through glycolysis. The energy-dependent transmembrane control is lost, with intracellular $K^+$ and $Mg^{2-}$ ions leaking out of the cells and extracellular $Na^-$ and $Ca^{2+}$ ions entering the cells. The redistribution of electrolytes leads to osmotic changes and cellular edema.

It is believed that several of the electrolytic changes that occur during ischemia may be responsible for cardiac arrhythmias. First, as noted above, during ischemia, intracellular $Na^+$ increases. During reperfusion, this results in depolarization and short action potentials combined with low extracellular $K^+$. Dispersion is pronounced and favorable to arrhythmias.

Second, systolic and mitochondrial $Ca^{2+}$ levels increase during ischemia and reperfusion. An increase in cystolic $Ca^{2+}$ activates a number of channels, carriers, and enzymes and modulates others, which results in delayed afterdepolarizations and arrhythmias.

Further, during ischemia, amphiphiles and fatty acids accumulate in the plasma membrane, the gap junction, and the intracellular membranes of the SR and the mitochondria. Amphiphiles and fatty acids may interact directly with channel proteins, with the phospholipids surrounding the channel proteins, or changing the membrane fluidity. Amphiphiles increase inward current at the resting potential with simultaneous reduction of outward current through $K^+$ channels. Fatty acids activate outward currents and stimulate the $K^+/Ca^{2+}$ exchanger. The simultaneous activation of inward and outward currents favors $K^+$ loss and $Ca^{2+}$ overload, creating conditions that generate arrhythmias. (Cameliet, 1999).

It is also believed that reperfusion injury may manifest clinically as reperfusion arrhythmias. Early reperfusion is an absolute prerequisite for the survival of ischemic tissue. Although ultimately necessary for recovery, reperfusion is often considered a double-edged sword, and can actually lead to worsening of tissue injury by various mechanisms. As with ischemia, reperfusion is associated with $Ca^{2+}$ overload through activation of the $K^+/Ca^{2+}$ exchanger, thereby creating conditions favorable to cardiac arrhythmias.

Complications associated with congestive heart failure include stress hyperglycemia and insulin resistance. As a result of the combination of high circulating levels of free fatty acids and reduced glucose uptake, there is a shift toward fatty acid oxidation. Again, these fatty acids can activate outward currents through $K^+$ channels, and stimulate the $K^+/Ca^{2+}$ exchanger. The simultaneous activation of inward and outward currents favors $K^+$ loss and $Ca^{2+}$ overload, thereby creating conditions favorable to the generation of arrhythmias.

GLP-1 and exendin are glucose-dependent insulinotropic peptides that effectively enhance peripheral glucose uptake without inducing dangerous hypoglycemia. Further, they strongly suppress glucagon secretion, independent of their insulinotropic action, and thereby powerfully reduce plasma free fatty acid (FFA) levels substantially more potently than can be accomplished with insulin (i.e., greater FFA suppression at equivalent prevailing insulin concentrations that are submaximally effective).

The present inventors have now discovered that GLP-1, exendins, and other compositions of the invention can be effective in the prevention and treatment of cardiac arrhythmias. It has now been found that the dual capacity of GLP-1 to powerfully stimulate insulin release and reduce insulin resistance provides this molecule with the unique ability to prevent and treat cardiac arrhythmias by enhancing glucose uptake and metabolism, at the expense of reduced FAA metabolism, into cardiac muscle. In this respect, incretins, GLP-1, exendins, compounds that bind a GLP-1 receptor, and agonists, analogs, derivatives, and variants thereof, as well as their active fragments can be especially effective in preventing and treating arrhythmias in patients with cardiac ischemia, cardiac ischemia-reperfusion, and/or congestive heart failure.

Treatment with GLP-1 and other compositions of the invention may enhance glycolysis in patients and shift the balance from fatty acid towards glucose oxidation.

These effects prevent loss of potassium and calcium overload, and reduce the risk of cardiac arrhythmias.

Compositions of the invention may also stimulate the secretion of endogenous insulin and therefore can be used to achieve all of the beneficial actions attributed to an insulin infusion in the metabolic treatment of arrhythmias. Although high-dose GIK infusions typically contain 25-33% glucose and 50-100 U insulin/L, the requirement for introduction of hyperglycemia per se to achieve therapeutic efficacy, versus only providing a metabolic milieu for the safe administration of high doses of insulin, is unclear. It is likely that adequate blood glucose levels are required to enable substrate delivery, but this does not necessarily imply a need for hyperglycemia and should not detract from the fact that insulin exerts important effects other than glucose uptake. Therefore, a therapeutic infusion of a composition of the invention, including GLP-1 and exendin, may require a modest (e.g., 5%) glucose administration in order to maintain blood glucose at slightly above physiological levels in order to trigger insulin release. Glucose is not required as a safety measure, since blood levels of ≦3.5 mM abrogate the insulin-stimulating activity of GLP-1 and exendin, thereby completely protecting against the dangers of hypoglycemia.

Insulin resistance (IR) has been recognized increasingly as a major pathogenic factor for multiple systemic diseases, and not only in individuals having Type-2 diabetes. Although many patients with Type-2 diabetes manifest insulin resistance, many individuals with IR do not have diabetes. An important recent insight has been the realization that IR is an independent risk factor for the development and severity of cardiovascular diseases, including ischemia-reperfusion injury and left ventricle dysfunction. IR is strongly associated with severe heart disease, both acutely and chronically, which leads to the enhanced and potentially damaging use by the heart of fatty acids as a fuel source in preference to glucose. Administration of GLP-1, exendin and other compositions of the invention, can reverse the use of fatty acids as fuel to glucose, thereby reducing free fatty acids and preventing the development of conditions favorable to the development of cardiac arrhythmias. The administration of GLP-1, exendin and other compositions of the invention may be especially effective in the treatment of ventricular arrhythmias.

The administration of GLP-1, exendin, and other compositions of the invention, should be effective in a majority of patients without requiring concurrent glucose administration. However, a small proportion of subjects may require glucose to elicit an adequate insulin response. In addition, it also may be necessary to administer potassium to correct excess shifts of potassium in the intracellular compartment when glucose is co-administered with compositions of the invention.

In addition to the use of GLP-1, exendin and other compositions of the invention, the methods of the invention can include use of free radical scavengers or anti-oxidants such as glutathione, melatonin, Vitamin E, and superoxide dismutase (SOD). In such combinations, reperfusion damage risk can be lessened even further.

Compositions of the invention include a compound that binds to a receptor for a glucagon like peptide-1, an incretin, a glucagon-like peptide-1 (GLP-1), an exendin, or an agonist, an analog (preferably an agonist analog), a derivative, or a variant of any of the aforementioned compounds, as well as biologically active fragments thereof. An "agonist" includes any compound that mimics at least one of the actions of an incretin, a GLP-1, or an exendin, as described herein.

An "analog" includes any peptide whose sequence was derived from that of the base receptor-binding compound, incretin, GLP-1, or exendin, whether or not including insertions, substitutions, extensions, or deletions, preferably having at least 50 or 55% amino acid sequence identity with the base molecule, more preferably having at least 70%, 80%, 90%, or 95% amino acid sequence identity with the base molecule. Such analogs may comprise conservative or non-conservative amino acid substitutions (including non-natural amino acids or as well as D forms), and if it is an "agonist analog," exhibits at least one characteristic of the base molecule, preferably having a potency better than the base molecule, or within five orders of magnitude of the base molecule, more preferably 4, 3, 2, or 1 order of magnitude when evaluated by art-known measures.

A "derivative" includes any base molecule or analog having a chemical modification within, attached or linked to, or associated with the molecule. Such chemical modifications can include internal linkers (e.g., spacing or structure-inducing) or appended molecules, such as molecular weight-enhancing molecules (e.g., polyethylene glycol (PEG)), or tissue targeting molecules. Examples of such molecules are known in the art, for example, insulinotropic peptides, including GLP-1 and exendin, modified with a maleimide group are described in U.S. Pat. No. 6,593,295, incorporated herein by reference.

A "variant" includes any modification to the base molecule, analog or variant not encompassed in the terms "analog" and "derivative," as would be known to a person of ordinary skill in the art. For example, variants may include proforms or chimeras of a selected molecule. Small molecules are included in the compounds useful in the invention to the extent that they bind to a receptor for GLP-1 or exendin.

Not all of the peptide molecules described as incretins, glucagon-like peptide-1 (GLP-1), exendins, or analogs, derivatives, or variants may bind to a receptor for GLP-1, although they are still useful in the invention by virtue of a pharmacology not dependent on a known GLP-1 receptor. These molecules may still possess the desired biological activities described herein. Other compounds encompassed within the scope of the invention include those described in U.S. Pat. Nos. 6,569,832; 6,528,486; 6,514,500; 6,458,924; 6,451,987; 6,451,974; 6,268,343, all herein incorporated by reference.

An example of a base molecule, as the term is used above, is GLP-1, also known as glucagon-like peptide-1 [7-36] amide (also referred to as GLP-1 [7-36]$NH_2$), a product of the proglucagon gene having the amino acid sequence His Ala Glu Gly Thr Phe Thr Ser Asp Val Ser Ser Tyr Leu Glu Gly Gln Ala Ala Lys Glu Phe Ile Ala Trp Leu Val Lys Gly Arg-$NH_2$ (SEQ ID NO:1). It is secreted into plasma mainly from the gut and produces a variety of biological effects related to pancreatic and gastrointestinal function.

Many functions of GLP-1[7-36]$NH_2$, "GLP-1," as used herein, are known (e.g., Orskov, et al., *Diabetes*, 42:658-61, 1993; D'Alessio, et al., *J. Clin. Invest.*, 97:133-38, 1996, Williams B, et al., *J Clin Endocrinol Metab* 81 (1): 327-32, 1996; Wettergren A, et al., *Dig Dis Sci* 38 (4): 665-73, 1993; Schjoldager B T, et al., *Dig Dis Sci* 34 (5): 703-8, 1989; O'Halloran D J, et al., *J Endocrinol* 126 (1): 169-73, 1990; Wettergren A, et al., *Dig Dis Sci* 38 (4): 665-73, 1993). GLP-1[7-37], which has an additional glycine residue at its carboxy terminus, also stimulates insulin secretion in humans (Orskov, et al., *Diabetes*, 42:658-61, 1993).

Compositions of the invention include GLP-1 agonist analogs. By "agonist analog" is meant a compound that mimics at least one effect of GLP-1 as described above. This definition of agonist analog could include compounds that bind to a receptor or receptors where GLP-1 causes the particular effect. Certain GLP-1 analogs with agonist activity are described in Chen et al., U.S. Pat. No. 5,512,549, issued Apr. 30, 1996, entitled Glucagon-Like Insulinotropic Peptide Analogs, Compositions and Methods of Use. Other GLP-1 analogs with agonist activity are described in Johnson et al., U.S. Pat. No. 5,574,008, issued Nov. 12, 1996, entitled, Biologically Active Fragments of Glucagon-Like Insulinotropic Peptide. Still other GLP-1 analogs with agonist activity are described in Buckley et al., U.S. Pat. No. 5,545,618, issued Aug. 13, 1996, entitled GLP-1 Analogs Useful for Diabetes Treatment. All three referenced U.S. patents are incorporated herein by this reference. The present invention includes the use of recombinant human GLP-1 analogs and GLP-1 analogs derived from other species, whether recombinant or synthetic.

In certain aspects, the GLP-1 agonist analogs used in the methods of the present invention can be GLP-1(7-34) and GLP-1(7-35), as disclosed in U.S. Pat. No. 5,118,666, herein incorporated by reference, as well as GLP-1(7-37) as disclosed in U.S. Pat. No. 5,120,712, herein incorporated by reference. Also included are GLP-1 analogs having a reduced tendency to aggregate such as those described in WO 01/98331; GLP-1 analogs that have N-terminal truncation, U.S. Pat. No. 5,574,008; GLP-1 analogs with attached acyl groups, U.S. Pat. No. 5,512,549; and GLP-1 analogs that are amidated, WO 02/48192; and GLP-1 analogs of U.S. patent application Ser. No. 10/276,772, all of which are incorporated by reference.

Additional analogs include, GLP-1 analogs at position 8, U.S. Pat. No. 5,981,488, incorporated by reference. In brief, analogs include those of formula (XI), $R_1$-X-Glu-Gly-Thr-Phe-Thr-Ser-Asp-Val-Ser-Ser-Tyr-Leu-Y-Gly-Gln-Ala-Ala- Lys-Z-Phe-Ile-Ala-Trp-Leu-Val-Lys-Gly-Arg-R$_2$ (SEQ ID NO:33) or a pharmacuetically accetable salt thereof, wherein:

R$_1$ is selected from the group consisting of His, D-histidine, desamino-histidine, 2-amino-histidine, .beta.-hydroxy-histidine, homohistidine, alpha-fluoromethyl-histidine, and alpha-methyl-histidine;

X is selected from the group consisting of Met, Asp, Lys, Thr, Leu, Asn, Gln, Phe, Val, and Tyr Y and Z are independently selected from the group consisting of Glu, Gln, Ala, Thr, Ser, and Gly, and;

R$_2$ is selected from the group consisting of NH$_2$, and Gly-OH; provided that, if R$_1$ is His, X is Val, Y is Glu, and Z is Glu, then R$_2$ is NH$_2$.

V8-GLP-1 and other position 8 analogs can be found in U.S. Pat. No. 5,705,483, incorporated by reference. In brief, analogs include those of formula (XII), R$_1$—X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-R$_2$ (SEQ ID NO: 34) wherein:

R$_1$ is selected from the group consisting of L-histidine, D-histidine, desamino-histidine, 2-amino-histidine, .beta.-hydroxy-histidine, homohistidine, alpha-fluoromethyl-histidine, and alpha-methyl-histidine;

X is selected from the group consisting of Ala, Gly, Val, Thr, Ile, and alpha-methyl-Ala;

Y is selected from the group consisting of Glu, Gln, Ala, Thr, Ser, and Gly;

Z is selected from the group consisting of Glu, Gln, Ala, Thr, Ser, and Gly;

R$_2$ is selected from the group consisting of NH$_2$, and Gly-OH; providing that the compound has an isoelectric point in the range from about 6.0 to about 9.0 and further providing that when R$_1$ is His, X is Ala, Y is Glu, and Z is Glu, R$_2$ must be NH$_2$.

In other aspects, the GLP-1 agonist analogs are variants or analogs of GLP-1 known in the art, such as, for example, Gln$^9$-GLP-1(7-37), D-Gln$^9$-GLP-1(7-37), acetyl-Lys$^9$-GLP-1(7-37), Thr$^{16}$-Lys$^{18}$-GLP-1(7-37), and Lys$^{18}$-GLP-1(7-37). Derivatives of GLP-1 are also contemplated in the present invention and include, for example, acid addition salts, carboxylate salts, lower alkyl esters, and amides (see, e.g., WO91/11457). Generally, the various forms of GLP-1 are known to stimulate insulin secretion (insulinotropic action) and cAMP formation (see, e.g., Mojsov, S., Int. J. Peptide Protein Research, 40:333-343 (1992)).

In still other aspects, the present invention contemplates GLP-1 agonists of the general formula (I):

(SEQ ID NO:2)

R$_1$-Ala-Glu-Gly-Thr-Phe-Thr-Ser-Asp-Val-Ser-Ser-Tyr-Leu-Glu-Gly-Gln-Ala-Ala-X*aa*$_{40}$-Glu-Phe-Ile-Ala-Trp-Leu-Val-Lsy-Gly-Arg-R$_3$
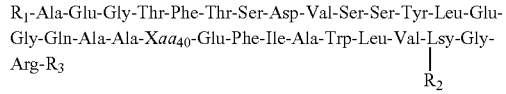

wherein R$_1$ is selected from the group consisting of 4-imidazopropionyl (des-amino-histidyl), 4-imidazoacetyl, or 4-imidazo-alpha, alpha dimethyl-acetyl;

R$_2$ is selected from the group consisting of C$_6$-C$_{10}$ unbranched acyl, or is absent;

R$_3$ is selected from the group consisting of Gly-OH or NH$_2$; and,

Xaa$_{40}$ is Lys or Arg.

In one embodiment, the GLP-1 agonists are naturally-occurring GLP-1(7-37) that arise from adding various R groups via a peptide bond to the amino terminus of the peptide portion of Formula I (SEQ ID NO:2). Optionally, further compounds of the invention are made by acylating the epsilon amino group of the Lys34 residue and by making limited amino acid substitutions at position 26 or by altering the carboxy terminus It should be noted that for the above formula, the nomenclature scheme used is that which has been developed around processed forms of GLP-1. In this scheme, the amino terminus of the known GLP-1(7-37) OH has been assigned number 7 and the carboxy terminus number 37. Therefore, the first Ala residue of Formula I corresponds to residue 8 of GLP-1 (7-37)OH. Likewise Xaa$_{40}$ in Formula I corresponds to residue 26 of GLP-1(7-37)OH, and so forth.

In still other aspects, the present invention provides biologically-active GLP-1 fragments of formula (II):

(SEQ ID NO: 3)
R$_4$-Ser-Tyr-Leu-Glu-Gly-Gln-Ala-Ala-Lys-Glu-

Phe-Ile-Ala-Trp-Leu-Val-Xaa$_{41}$-Gly-Arg-R$_5$ wherein R$_4$ is selected from the group consisting of:
a) H$_2$N;
b) H$_2$N-Ser;
c) H$_2$N-Val-Ser;
d) H$_2$N-Asp-Val-Ser;
e) H$_2$N-Ser-Asp-Val-Ser (SEQ ID NO:4);
f) H$_2$N-Thr-Ser-Asp-Val-Ser (SEQ ID NO:5);
g) H$_2$N-Phe-Thr-Ser-Asp-Val-Ser (SEQ ID NO:6);
h) H$_2$N-Thr-Phe-Thr-Ser-Asp-Val-Ser (SEQ ID NO:7);
i) H$_2$ N-Gly-Thr-Phe-Thr-Ser-Asp-Val-Ser (SEQ ID NO:8);
j) H$_2$ N-Glu-Gly-Thr-Phe-Thr-Ser-Asp-Val-Ser (SEQ ID NO:9); or
k) H$_2$ N-Ala-Glu-Gly-Thr-Phe-Thr-Ser-Asp-Val-Ser (SEQ ID NO:10);

Xaa$_{41}$ is selected from the group consisting of Lys or Arg; and wherein R$_5$ is selected from the group consisting of NH$_2$, OH, Gly-NH$_2$, or Gly-OH.

In still other aspects, the invention provides modified forms of the GLP-1(7-34); (7-35); (7-36) or (7-37) human peptide or the C-terminal amidated forms thereof. The native peptides have the amino acid sequence (SEQ ID NO:11):

```
      7        10          15          20          25
      H-A-E-G-T-F-T-S-D-V-S-S-Y-L-E-G-Q-A-A-K-E-F 30                37
              -I-A-W-L-V-K-(G)-(R)-(G)
``` wherein (G), (R), and (G) are present or absent depending on the indicated chain length. The modified forms contain one or more alterations of the native structure and are of improved ability for therapeutic use. Either the modified forms have greater potency than glucagon to potentiate insulin secretion or enhanced stability in plasma or both.

The analogs of the invention which show enhanced insulin stimulating properties may have the foregoing sequence, or a C-terminal amide thereof, with at least one modification of SEQ ID NO:11, selected from the group consisting of:

(a) substitution of a neutral amino acid, arginine, or a D form of lysine for lysine at position 26 and/or 34 and/or a neutral amino acid, lysine, or a D form of arginine for arginine at position 36;

(b) substitution of an oxidation-resistant amino acid for tryptophan at position 31;

(c) substitution according to at least one of:
    Y for V at position 16;
    K for S at position 18;
    D for E at position 21;
    S for G at position 22;
    R for Q at position 23;
    R for A at position 24; and
    Q for K at position 26;
(d) a substitution comprising at least one of:
    an alternative small neutral amino acid for A at position 8;
    an alternative acidic amino acid or neutral amino acid for E at position 9;
    an alternative neutral amino acid for G at position 10; and
    an alternative acidic amino acid for D at position 15; and
(e) substitution of an alternative neutral amino acid or the D or N-acylated or alkylated form of histidine for histidine at position 7.

With respect to modifications (a), (b), (d) and (e), the substituted amino acids may be in the D form, as indicated by a superscript †, e.g., $C^†$. The amino acids substituted at position 7 can also be in the N-acylated or N-alkylated forms.

In another aspect, the invention is directed to peptides which show enhanced degradation resistance in plasma as compared to GLP-1(7-37) wherein this enhanced resistance to degradation is defined as set forth below. In these analogs, any of the above-mentioned truncated forms of GLP-1(7-34) to GLP-1(7-37) or their C-terminal amidated form is modified by
(a) substitution of a D-neutral or D-acidic amino acid for H at position 7, or
(b) substitution of a D-amino acid for A at position 8, or
(c) both, or
(d) substitution of an N-acylated or N-alkylated form of any naturally occurring amino acid for H at position 7.

Thus, analogs of the invention which are resistant to degradation include (N-acyl (1-6C) AA)$^7$ GLP-1(7-37) and (N-alkyl (1-6C) AA)$^7$ GLP-1(7-37) wherein when AA is a lysyl residue, one or both nitrogens may be alkylated or acylated. AA symbolizes any amino acid consistent with retention of insulin stimulating activity.

For substitutions of D-amino acids in the 7 and 8 positions of SEQ ID NO:11, the D residue of any acidic or neutral amino acid can be used at position 7 and of any amino acid at position 8, again consistent with insulin stimulating activity. Either or both of position 7 and 8 can be substituted by a D-amino acid; the D-amino acid at position 7 can also be acylated or alkylated as set forth above. These modified forms are applicable not only to GLP-1(7-37) but also the shorter truncated analogs as set forth above.

Other modified GLP-1s, as well as exendins, useful in the practice of the claimed invention can be found in U.S. Pat. No. 6,528,486, which is incorporated by reference.

As previously stated, GLP-1 analogs, as well as exendin analogs, may be peptides containing one or more amino acid substitutions, additions, extensions, or deletions, compared with GLP-1(7-36)amide, exendin-4 or exendin-3. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue as is well known in the art. Examples of conservative substitutions include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like.

It is further understood that GLP-1 analogs include the above described peptides which have been chemically derivatized or altered, for example, peptides with non-natural amino acid residues (e.g., taurine, β- and γ-amino acid residues and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid. Exendin analogs may have similar modifications.

Also included in the present invention are peptide sequences having greater than 50% or 55% amino acid sequence identity, and preferably greater than 70, 80, 90, or 95% amino acid sequence identity to SEQ ID NOs:1, 12, and 14, as well as truncated sequences thereof. As used herein, sequence identity refers to a comparison made between two molecules using standard algorithms well known in the art. The preferred algorithm for calculating sequence identity for the present invention is the Smith-Waterman algorithm, for example, SEQ ID NO: 1 [i.e., GLP-1(1-37)], SEQ ID NO:12 or 14 [exendin-3 and 4, respectively] can be used as the reference sequences to define the percentage identity of homology over their length. The choice of parameter values for matches, mismatches, and insertions or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid). Waterman, *Bull. Math. Biol.* 46; 473 (1984). Insertions and deletions (indels), x, are weighted as $x_k=1+⅓k$, where k is the number of residues in a given insert or deletion. Id.

For instance, a sequence that is identical to the 37-amino acid residue sequence of SEQ ID NO: 1, except for 18 amino acid substitutions and an insertion of 3 amino acids, would have a percent identity given by:

$$[(1×37 \text{ matches})−(⅓×18 \text{ mismatches})−(1+3/3 \text{ indels})]/37=78\% \text{ "identity."}$$

This algorithm can be used with any amino acid sequence to determine sequence homology.

Agonists of glucagon-like peptide that exhibit activity through a GLP-1(7-36)amide receptor have been described. See EP 0708179 A2; Hjorth et al., *J. Biol. Chem.* 269; 30121 (1994); Siegel et al., Amer. Diabetes Assoc. 57$^{th}$ Scientific Session, Boston (1997); Hareter et al., Amer. Diabetes Assoc. 57$^{th}$ Scientific Session, Boston (1997); Adelhorst et al., *J. Biol. Chem.* 269, 6275 (1994); Deacon et al., 16$^{th}$ International Diabetes Federation Congress Abstracts, *Diabetologia Supplement* (1997); Irwin et al., *Proc. Natl. Acad. Sci. USA* 94; 7915 (1997); Mojsov, *Int. J. Peptide Protein Res.* 40; 333 (1992). Göke & Byrne, *Diabetic Medicine* 13; 854 (1996). Recent publications disclose Black Widow GLP-1 and Ser$^2$ GLP-1. See Holz & Hakner, *Comp. Biochem. Physiol.*, Part B 121; 177 (1998) and Ritzel et al., *J. Endocrinol* 159; 93 (1998).

GLP-1 receptors are cell-surface proteins found, for example, on insulin-producing pancreatic β-cells; the GLP-1(7-36) receptor has been characterised in the art. Additional receptors at which GLP-1 and exendins act are also thought to exist, and may mediate effects by which the instant invention is operative. Methods of determining whether a chemical or peptide binds to or activates a particular GLP-1 receptor are known to the skilled artisan. For example, U.S. Pat. Nos. 6,051,689, 5,846,747, and 5,670,360 describe GLP-1 receptors, as well as methods for using them. The contents of the patents are incorporated by reference.

The biological activity of a GLP-1 agonist and/or analog can be determined by in vitro and in vivo animal models and human studies, as is well known to the skilled artisan. GLP-1 biological activity can be determined by standard methods, in general, by receptor binding activity screening procedures, which involve providing appropriate cells that express the GLP-1 receptor on their surface, for example, insulinoma cell lines such as RINmSF cells or INS-1 cells. See Mojsov, *Int. J. Peptide Protein Res.* 40; 333 (1992) and EP 0708179 A2. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding a GLP-1 receptor is employed to transfect cells so that they express the GLP-1 receptor protein. Thus, for example, these methods may be employed for screening for a receptor agonist by contacting such cells with compounds to be screened and determining whether such compounds generate a signal (i.e., activate the receptor). Other screening techniques include the use of cells that express the GLP-1 receptor, for example, transfected CHO cells, in a system to measure extracellular pH or ionic changes caused by receptor activation. For example, potential agonists may be contacted with a cell that expresses the GLP-1 protein receptor and a second messenger response (e.g., signal transduction or ionic or pH changes), may be measured to determine whether the potential agonist is effective.

Polyclonal and monoclonal antibodies can be utilized to detect, purify, and identify GLP-1-like peptides for use in the methods described herein. Antibodies such as ABGA1178 detect intact GLP-1(1-37) or N-terminally-truncated GLP-1 (7-37) or GLP-1(7-36)amide. Other antibodies detect the end of the C-terminus of the precursor molecule, a procedure that allows one—by subtraction—to calculate the amount of biologically active, truncated peptide (i.e., GLP-1(7-37)amide). Orskov et al., *Diabetes* 42; 658 (1993); Orskov et al., *J. Clin. Invest.* 1991, 87; 415 (1991).

GLP-1, its agonists, analogs, derivatives, variants, and biologically active fragments, that are peptides can be made by solid-state chemical peptide synthesis. Such peptides can also be made by conventional recombinant techniques using standard procedures described in, for example, Sambrook & Maniatis, Molecular Cloning, A Laboratory Manual. "Recombinant," as used herein, means that a gene is derived from a recombinant (e.g., microbial or mammalian) expression system that has been genetically modified to contain a polynucleotide encoding a GLP-1 peptide as described herein.

GLP-1, its agonists, analogs, derivatives, variants, and biologically active fragments, that are peptides may be a naturally purified product, or a product of synthetic chemical procedures, or produced by recombinant techniques from prokaryotic or eukaryotic hosts (for example, by bacteria, yeast, higher plant, insect, or mammalian cells in culture or in vivo). Depending on the host employed in a recombinant production procedure, the polypeptides of the present invention are generally non-glycosylated, but may be glycosylated. The GLP-1 peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High-performance liquid chromatography (HPLC) can be employed for final purification steps.

Other compositions of the invention include exendins, which refer to naturally occurring exendin peptides that are found in Gila-monster. Preferred exendins include exendin-3 (SEQ ID NO:12), which is present in the salivary secretions of Heloderma harridum, exendin-4 (SEQ ID NO:14), which is a peptide present in the salivary secretions of Heloderma suspectum (Eng, J., et al., *J. Biol. Chem.*, 265:20259-62, 1990; Eng., J., et al., *J. Biol. Chem.*, 267:7402-05, 1992), and agonists, analogs, derivative, variants of either of them as well as biologically active fragments thereof. Exendin-4, as it occurs in the salivary secretions of the Gila monster, is an amidated peptide. However, it should be understood that the term "exendin," "exendin-3," and "exendin-4" refer to both the amidated form of the peptide and the acid form of the peptide. Likewise, reference to GLP-1 generally refers to the amidated 7-36 molecule, but it is also intended to include non-amidated molecules.

"Exendin agonist" refers to compounds that mimic any effect of an exendin by binding to the receptor or receptors where a naturally occurring exendin exerts an effect. Exendin "agonist activity" in this context means having a biological activity of an exendin, such as those described herein; but it is understood that the activity of the agonist can be either less potent or more potent than the native exendin.

Exendin-4 is a 39-amino acid polypeptide. Certain sequences are compared in Table 1.

TABLE 1 a. HAEGTFTSDVSSYLEGQAAKEFIAWLVKGR (NH$_2$)

b. HSDGTFTSDLSKQMEEEAVRLFIEWLKNGGPSSGAPPPS (NH$_2$)

c. DLSKQMEEEAVRLFIEWLKNGGPSSGAPPPS (NH$_2$)

d. HGEGTFTSDLSKQMEEEAVRLFIEWLKNGGPSSGAPPPS (NH$_2$)

e. HSDATFTAEYSKLLAKLALQKYLESILGSSTSPRPPSS f. HSDATFTAEYSKLLAKLALQKYLESILGSSTSPRPPS g. HSDAIFTEEYSKLLAKLALQKYLASILGSRTSPPP (NH$_2$)

h. HSDAIFTQQYSKLLAKLALQKYLASILGSRTSPPP (NH$_2$)

a = GLP-1(7-36) (NH$_2$) [SEQ ID NO: 1].
b = exendin 3 (NH$_2$) [SEQ ID NO: 12].
c = exendin 4 (9-39)(NH$_2$) [SEQ ID NO: 13].
d = exendin 4 (NH$_2$) [SEQ ID NO: 14].
e = helospectin I [SEQ ID NO: 15].
f = helospectin II [SEQ ID NO: 16].
g = helodermin (NH$_2$) [SEQ ID NO: 17].
h = Q$^8$, Q$^9$ helodermin (NH$_2$) [SEQ ID NO: 18].

Various experiments have compared the biologic actions of exendin-4 and GLP-1 and demonstrated a more favorable spectrum of properties for exendin-4. A single subcutaneous dose of exendin-4 lowered plasma glucose in db/db (diabetic) and ob/ob (diabetic obese) mice by up to 40%. In Diabetic Fatty Zucker (ZDF) rats, 5 weeks of treatment with exendin-4 lowered HbA$_{1c}$ (a measure of glycosylated hemoglobin used to evaluate plasma glucose levels) by up to 41%. Insulin sensitivity was also improved by 76% following 5 weeks of treatment in obese ZDF rats. In glucose intolerant primates, dose-dependent decreases in plasma glucose were also observed.

An insulinotropic action of exendin-4 has also been observed in rodents, improving insulin response to glucose by over 100% in non-fasted Harlan Sprague Dawley (HSD) rats, and by up to ~10-fold in non-fasted db/db mice. Higher pretreatment plasma glucose concentrations were associated with greater glucose-lowering effects. Thus the observed glucose lowering effect of exendin-4 appears to be glucose-dependent, and minimal if animals are already euglycemic. Degradation studies with exendin-4 compared to GLP-1 indicate that exendin-4 is relatively resistant to degradation.

As used in this specification, the term "exendin agonist" includes any molecules, whether they be peptides, peptide mimetics, or other chemical compounds, that bind to or activate a receptor or receptors at which exendin exerts an effect, as described above. Moreover, exendin agonists may include molecules having insulinotropic activity and that may bind a GLP-1 receptor molecule in in vitro assays and induce second messenger activity on, inter alia, insulin producing β-cells.

The structure activity relationship (SAR) of exendin was investigated for structures that may relate to the activity of exendin, for its stability to metabolism, and for improvement of its physical characteristics, especially as it pertains to peptide stability and to amenability to alternative delivery systems, and various exendin agonist peptide compounds have been invented. Exendin agonists include exendin analogs with agonist activity in which one or more naturally or non-naturally occurring amino acids are added, inserted, eliminated or replaced with another amino acid(s). Preferred exendin analogs are peptide analogs of exendin-4.

Exendin analogs include peptides that are encoded by polynucleotides that express biologically active exendin analogs with agonist activity, as defined herein. For instance, exendin analogs may be peptides containing one or more amino acid substitutions, extensions, additions or deletions, compared with exendin-4 or exendin-3. In one embodiment, the number of substitutions, extension, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. Exendin analogs, which include chemically derivatized or altered compounds and peptides having a preferred amino acid homology to SEQ ID NOs:12 and 14 have been previously described and are contemplated to be within the scope of the claimed invention.

Novel exendin analogs with agonist activity are described in PCT Application Serial No. PCT/US98/16387 filed Aug. 6, 1998, entitled "Novel Exendin Agonist Compounds," which claims the benefit of U.S. Patent Application Ser. No. 60/055, 404, filed Aug. 8, 1997, both of which are herein incorporated by reference.

Other novel exendin analogs with agonist activity are described in PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997, both of which are herein incorporated by reference.

Still other novel exendin analogs with agonist activity are described in PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997, both of which are herein incorporated by reference.

Still other exendin analogs with agonist activity are described in PCT Application Serial No. PCT/US97/14199, filed Aug. 8, 1997, entitled "Methods for Regulating Gastrointestinal Activity," which is a continuation-in-part of U.S. patent application Ser. No. 08/694,954 filed Aug. 8, 1996, both of which are hereby incorporated by reference.

Still other exendin analogs with agonist activity are described in PCT Application Serial No. PCT/US98/00449, filed Jan. 7, 1998, entitled "Use of Exendins and Agonists Thereof for the Reduction of Food Intake," which claims priority to U.S. Provisional Application No. 60/034,905 filed Jan. 7, 1997, both of which are hereby incorporated by reference.

Activity as exendin agonists and exendin analogs with agonist activity can be indicated, for example, by activity in the assays incorporated by reference in the referenced applications. Effects of exendins or exendin agonists can be identified, evaluated, or screened for, using the methods described herein, or other art-known or equivalent methods for determining the effects of exendin. Screening assays for potential exendin agonist compounds or candidate exendin agonist compounds, may include an in vitro GLP-1 receptor assay/screen described above, an amylin receptor assay/screen using an amylin receptor preparation as described in U.S. Pat. No. 5,264,372, issued Nov. 23, 1993, the contents of which are incorporated herein by reference, one or more calcitonin receptor assays/screens using, for example, T47D and MCF7 breast carcinoma cells, which contain calcium receptors coupled to the stimulation of adenyl cyclase activity, and/or a CGRP receptor assay/screen using, for example, SK-N-MC cells.

Certain preferred exendin analogs with agonist activity include:

```
exendin-4 (1-30) [SEQ ID NO: 19:
His Gly Glu Gly Thr Phe Thr Ser Asp Leu Ser Lys Gln Met Glu Glu Glu Ala Val Arg Leu Phe Ile Glu Trp Leu Lys Asn Gly Gly];

exendin-4 (1-30) amide [SEQ ID NO: 20:
His Gly Glu Gly Thr Phe Thr Ser Asp Leu Ser Lys Gln Met Glu Glu Glu Ala Val Arg Leu Phe Ile Glu Trp Leu Lys Asn Gly Gly-NH₂];

exendin-4 (1-28) amide [SEQ ID NO: 21:
His Gly Glu Gly Thr Phe Thr Ser Asp Leu Ser Lys Gln Met Glu Glu Glu Ala Val Arg Leu Phe Ile Glu Trp Leu Lys Asn-NH₂];

¹⁴Leu,²⁵Phe exendin-4 amide [SEQ ID NO: 22:
His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH₂];

¹⁴Leu,²⁵Phe exendin-4 (1-28) amide [SEQ ID NO: 23:
His Gly Glu Gly Thr Phe Thr Ser Asp Leu Ser Lys Gln Leu Glu Glu Glu Ala Val Arg Leu Phe Ile Glu Phe Leu Lys Asn-NH₂];
and ¹⁴Leu,²²Ala,²⁵Phe exendin-4 (1-28) amide
[SEQ ID NO: 24:
His Gly Glu Gly Thr Phe Thr Ser Asp Leu Ser Lys Gln Leu Glu Glu Glu Ala Val Arg Leu Ala Ile Glu Phe Leu Lys Asn-NH₂].
```

Also included within the scope of the present invention are pharmaceutically acceptable salts of the compounds of formula (III-X) and pharmaceutical compositions including said compounds and salts thereof.

Formula III

Exendin analogs with agonist activity also include those described in U.S. Provisional Application No. 60/065,442, including compounds of the formula (III) [SEQ ID NO. 25]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein
- $Xaa_1$ is His, Arg or Tyr;
- $Xaa_2$ is Ser, Gly, Ala or Thr;
- $Xaa_3$ is Ala, Asp or Glu;
- $Xaa_5$ is Ala or Thr;
- $Xaa_6$ is Ala, Phe, Tyr or naphthylalanine;
- $Xaa_7$ is Thr or Ser;
- $Xaa_8$ is Ala, Ser or Thr;
- $Xaa_9$ is Asp or Glu;
- $Xaa_{10}$ is Ala, Leu, Ile, Val, pentylglycine or Met;
- $Xaa_{11}$ is Ala or Ser;
- $Xaa_{12}$ is Ala or Lys;
- $Xaa_{13}$ is Ala or Gln;
- $Xaa_{14}$ is Ala, Leu, Ile, pentylglycine, Val or Met;
- $Xaa_{15}$ is Ala or Glu;
- $Xaa_{16}$ is Ala or Glu;
- $Xaa_{17}$ is Ala or Glu;
- $Xaa_{19}$ is Ala or Val;
- $Xaa_{20}$ is Ala or Arg;
- $Xaa_{21}$ is Ala or Leu;
- $Xaa_{22}$ is Ala, Phe, Tyr or naphthylalanine;
- $Xaa_{23}$ is Ile, Val, Leu, pentylglycine, tert-butylglycine or Met;
- $Xaa_{24}$ is Ala, Glu or Asp;
- $Xaa_{25}$ is Ala, Trp, Phe, Tyr or naphthylalanine;
- $Xaa_{26}$ is Ala or Leu;
- $Xaa_{27}$ is Ala or Lys;
- $Xaa_{28}$ is Ala or Asn;
- $Z_1$ is —OH,
  —$NH_2$
  Gly-$Z_2$,
  Gly Gly-$Z_2$,
  Gly Gly $Xaa_{31}$-$Z_2$,
  Gly Gly $Xaa_{31}$ Ser-$Z_2$,
  Gly Gly $Xaa_{31}$ Ser Ser-$Z_2$, (SEQ ID NO: 35)
  Gly Gly $Xaa_{31}$ Ser Ser Gly-$Z_2$, (SEQ ID NO: 36)
  Gly Gly $Xaa_{31}$ Ser Ser Gly Ala-$Z_2$, (SEQ ID NO: 37)
  Gly Gly $Xaa_{31}$ Ser Ser Gly Ala $Xaa_{36}$-$Z_2$, (SEQ ID NO: 38)
  Gly Gly $Xaa_{31}$ Ser Ser Gly Ala $Xaa_{36}$ $Xaa_{37}$-$Z_2$ (SEQ ID NO: 39) or
  Gly Gly $Xaa_{31}$ Ser Ser Gly Ala $Xaa_{36}$ $Xaa_{37}$ $Xaa_{38}$-$Z_2$; (SEQ ID NO: 401
- $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and
- $Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin analogs include those wherein $Xaa_1$ is His or Tyr. More preferably $Xaa_1$ is His.

Preferred are those compounds wherein $Xaa_2$ is Gly.

Preferred are those compounds wherein $Xaa_{14}$ is Leu, pentylglycine or Met.

Preferred compounds are those wherein $Xaa_{25}$ is Trp or Phe.

Preferred compounds are those where $Xaa_6$ is Phe or naphthylalanine; $Xaa_{22}$ is Phe or naphthylalanine and $Xaa_{23}$ is Ile or Val.

Preferred are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.

Preferably $Z_2$ is —$NH_2$.

According to one aspect, preferred are compounds of formula (III) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (III) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$ (SEQ ID NO: 42), Gly Gly $Xaa_{31}$ Ser Ser Gly-$Z_2$ (SEQ ID NO: Gly Gly $Xaa_{31}$ Ser Ser Gly Ala-$Z_2$ (SEQ ID NO: 44), Gly Gly $Xaa_{31}$ Ser Ser Gly Ala $Xaa_{36}$-$Z_2$ (SEQ ID NO: 45), Gly Gly $Xaa_{31}$ Ser Ser Gly Ala $Xaa_{36}$ $Xaa_{37}$-$Z_2$ (SEQ ID NO: Gly Gly $Xaa_{31}$ Ser Ser Gly Ala $Xaa_{36}$ $Xaa_{37}$ $Xaa_{38}$-$Z_2$ (SEQ ID NO: 47); $Xaa_{31}$, $Xaa_{36}$, $Xaa_{37}$ and $Xaa_{38}$ being independently Pro, homoproline, thioproline or N-methylalanine; and $Z_2$ being —OH or —$NH_2$; provided that no more than three of $Xaa_3$, $Xaa_5$, $Xaa_6$, $Xaa_5$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Especially preferred compounds include those set forth in PCT application Serial No. PCT/US98/24210, filed Nov. 13, 1998, entitled "Novel Exendin Agonist Compounds" identified therein as compounds 2-23.

According to an especially preferred aspect, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degration, both in vitro and in vivo, as well as during synthesis of the compound.

Formula IV

Exendin analogs with agonist activity also include those described in U.S. Provisional Application No. 60/066,029, including compounds of the formula (IV)[SEQ ID NO. 26]:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

Xaa$_{27}$ Xaa$_{28}$-Z$_1$;

wherein:
- Xaa$_1$ is His, Arg, Tyr, Ala, Norval, Val or Norleu;
- Xaa$_2$ is Ser, Gly, Ala or Thr;
- Xaa$_3$ is Ala, Asp or Glu;
- Xaa$_4$ is Ala, Norval, Val, Norleu or Gly;
- Xaa$_5$ is Ala or Thr;
- Xaa$_6$ is Phe, Tyr or naphthylalanine;
- Xaa$_7$ is Thr or Ser;
- Xaa$_8$ is Ala, Ser or Thr;
- Xaa$_9$ is Ala, Norval, Val, Norleu, Asp or Glu;
- Xaa$_{10}$ is Ala, Leu, Ile, Val, pentylglycine or Met;
- Xaa$_{11}$ is Ala or Ser;
- Xaa$_{12}$ is Ala or Lys;
- Xaa$_{13}$ is Ala or Gln;
- Xaa$_{14}$ is Ala, Leu, Ile, pentylglycine, Val or Met;
- Xaa$_{15}$ is Ala or Glu;
- Xaa$_{16}$ is Ala or Glu;
- Xaa$_{17}$ is Ala or Glu;
- Xaa$_{19}$ is Ala or Val;
- Xaa$_{20}$ is Ala or Arg;
- Xaa$_{21}$ is Ala or Leu;
- Xaa$_{22}$ is Phe, Tyr or naphthylalanine;
- Xaa$_{23}$ is Ile, Val, Leu, pentylglycine, tert-butylglycine or Met;
- Xaa$_{24}$ is Ala, Glu or Asp;
- Xaa$_{25}$ is Ala, Trp, Phe, Tyr or naphthylalanine;
- Xaa$_{26}$ is Ala or Leu;
- Xaa$_{27}$ is Ala or Lys;
- Xaa$_{28}$ is Ala or Asn;
- Z$_1$ is —OH,
- —NH$_2$,
- Gly-Z$_2$,
- Gly Gly-Z$_2$,
- Gly Gly Xaa$_{31}$-Z$_2$,
- Gly Gly Xaa$_{31}$ Ser-Z$_2$,
- Gly Gly Xaa$_{31}$ Ser Ser-Z$_2$, (SEQ ID NO: 35)
- Gly Gly Xaa$_{31}$ Ser Ser Gly-Z$_2$, (SEQ ID NO: 36)
- Gly Gly Xaa$_{31}$ Ser Ser Gly Ala-Z$_2$, (SEQ ID NO: 37)
- Gly Gly Xaa$_{31}$ Ser Ser Gly Ala Xaa$_{36}$-Z$_2$, (SEQ ID NO: 38)
- Gly Gly Xaa$_{31}$ Ser Ser Gly Ala Xaa$_{36}$ Xaa$_{37}$-Z$_2$, (SEQ ID NO: 39)
- Gly Gly Xaa$_{31}$ Ser Ser Gly Ala Xaa$_{36}$ Xaa$_{37}$ Xaa$_{38}$-Z$_2$ (SEQ ID NO: 40) or
- Gly Gly Xaa$_{31}$ Ser Ser Gly Ala Xaa$_{36}$ Xaa$_{37}$ Xaa$_{38}$ Xaa$_{39}$-Z$_2$; (SEQ ID NO: 41)
- Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; and
- Z$_2$ is —OH or —NH$_2$;

provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that, if Xaa$_1$ is His, Arg or Tyr, then at least one of Xaa$_3$, Xaa$_4$ and Xaa$_9$ is Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (II) include those described in application Serial No. PCT/US98/24273, filed Nov. 13, 1998, entitled "Novel Exendin Agonist Compounds", identified therein in Examples 1-89 ("Compounds 1-89," respectively), as well as those corresponding compounds identified therein in Examples 104 and 105.

Preferred such exendin analogs include those wherein Xaa$_1$ is His, Ala or Norval. More preferably Xaa$_1$ is His or Ala. Most preferably Xaa$_1$ is His.

Preferred are those compounds of formula (IV) wherein Xaa$_2$ is Gly.

Preferred are those compounds of formula (IV) wherein Xaa$_3$ is Ala.

Preferred are those compounds of formula (IV) wherein Xaa$_4$ is Ala.

Preferred are those compounds of formula (IV) wherein Xaa$_9$ is Ala.

Preferred are those compounds of formula (IV) wherein Xaa$_{14}$ is Leu, pentylglycine or Met.

Preferred compounds of formula (IV) are those wherein Xaa$_{25}$ is Trp or Phe.

Preferred compounds of formula (IV) are those where Xaa$_6$ is Ala, Phe or naphthylalanine; Xaa$_{22}$ is Phe or naphthylalanine; and Xaa$_{23}$ is Ile or Val.

Preferred are compounds of formula (IV) wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.
Preferably Z$_2$ is —NH$_2$.

According to one aspect, preferred are compounds of formula (IV) wherein Xaa$_1$ is Ala, His or Tyr, more preferably Ala or His; Xaa$_2$ is Ala or Gly; Xaa$_6$ is Phe or naphthylalanine; Xaa$_{14}$ is Ala, Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more preferably Ser. More preferably Z$_1$ is —NH$_2$.

According to an especially preferred aspect, especially preferred compounds include those of formula (IV) wherein: Xaa$_1$ is His or Ala; Xaa$_2$ is Gly or Ala; Xaa$_3$ is Ala, Asp or Glu; Xaa$_4$ is Ala or Gly; Xaa$_5$ is Ala or Thr; Xaa$_6$ is Phe or naphthylalanine; Xaa$_7$ is Thr or Ser; Xaa$_8$ is Ala, Ser or Thr; Xaa$_9$ is Ala, Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu, Met or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_3$, Ser-Z$_2$, Gly Gly Xaa$_{31}$ Ser Ser-Z$_2$ (SEQ ID NO: 42), Gly Gly Xaa$_{31}$ Ser Ser Gly-Z$_2$ fSEO ID NO: 43), Gly Gly Xaa$_{31}$ Ser Ser Gly Ala-Z$_2$ (SEQ ID NO: Gly Gly Xaa$_{31}$ Ser Ser Gly Ala Xaa$_{36}$-Z$_2$ (SEQ ID NO: 45], Gly Gly Xaa$_3$, Ser Ser Gly Ala Xaa$_{36}$ Xaa$_{37}$-Z$_2$ (SEQ ID NO: 46), Gly Gly Xaa$_{31}$ Ser Ser Gly Ala Xaa$_{36}$ Xaa$_{37}$ Xaa$_{38}$-Z$_2$ (SEQ ID NO: 47) or Gly Gly Xaa$_{31}$ Ser Ser Gly Ala Xaa$_{36}$ Xaa$_{37}$ Xaa$_{38}$ Xaa$_{39}$-Z$_2$ (SEQ ID NO: 49); Xaa$_{31}$, Xaa$_{36}$, Xaa$_{37}$ and Xaa$_{38}$ being independently Pro, homoproline, thioproline or N-methylalanine; and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that, if Xaa$_1$ is His, Arg or Tyr, then at least one of Xaa$_3$, Xaa$_4$ and Xaa$_9$ is Ala. Especially preferred compounds of formula (IV) include those described in application Serial No. PCT/US98/

24273, filed Nov. 13, 1998, entitled "Novel Exendin Agonist Compounds" as having the amino acid sequence of SEQ. ID. NOS. 5-93 therein.

According to an especially preferred aspect, provided are compounds of formula (IV) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula V

Also within the scope of the present invention are narrower genera of compounds having peptides of various lengths, for example genera of compounds which do not include peptides having a length of 28, 29 or 30 amino acid residues, respectively. Additionally, the present invention includes narrower genera of compounds described in PCT application Serial No. PCT/US98/24210, filed Nov. 13, 1998, entitled "Novel Exendin Agonist Compounds" and having particular amino acid sequences, for example, compounds of the formula (V) [SEQ. ID. NO. 27]:

```
Xaa₁ Xaa₂ Xaa₃ Gly Xaa₅ Xaa₆ Xaa₇ Xaa₈ Xaa₉ Xaa₁₀

Xaa₁₁ Xaa₁₂ Xaa₁₃ Xaa₁₄ Xaa₁₅ Xaa₁₆ Xaa₁₇ Ala

Xaa₁₉ Xaa₂₀ Xaa₂₁ Xaa₂₂ Xaa₂₃ Xaa₂₄ Xaa₂₅ Xaa₂₆

Xaa₂₇ Xaa₂₈-Z₁;
``` wherein:
  $Xaa_1$ is His or Arg;
  $Xaa_2$ is Gly or Ala;
  $Xaa_3$ is Ala, Asp or Glu;
  $Xaa_5$ is Ala or Thr;
  $Xaa_6$ is Ala, Phe or naphthylalanine;
  $Xaa_7$ is Thr or Ser;
  $Xaa_8$ is Ala, Ser or Thr;
  $Xaa_9$ is Asp or Glu;
  $Xaa_{10}$ is Ala, Leu or pentylglycine;
  $Xaa_{11}$ is Ala or Ser;
  $Xaa_{12}$ is Ala or Lys;
  $Xaa_{13}$ is Ala or Gln;
  $Xaa_{14}$ is Ala, Leu or pentylglycine;
  $Xaa_{15}$ is Ala or Glu;
  $Xaa_{16}$ is Ala or Glu;
  $Xaa_{17}$ is Ala or Glu;
  $Xaa_{19}$ is Ala or Val;
  $Xaa_{20}$ is Ala or Arg;
  $Xaa_{21}$ is Ala or Leu;
  $Xaa_{22}$ is Phe or naphthylalanine;
  $Xaa_{23}$ is Ile, Val or tert-butylglycine;
  $Xaa_{24}$ is Ala, Glu or Asp;
  $Xaa_{25}$ is Ala, Trp, or Phe;
  $Xaa_{26}$ is Ala or Leu;
  $Xaa_{27}$ is Ala or Lys;
  $Xaa_{28}$ is Ala or Asn;
  $Z_1$ is —OH,
    —NH₂,
    Gly-Z₂,
    Gly Gly-Z₂,
    Gly Gly $Xaa_{31}$-Z₂,
    Gly Gly $Xaa_{31}$ Ser-Z₂,
    Gly Gly $Xaa_{31}$ Ser Ser-Z₂, (SEQ ID NO: 42)
    Gly Gly $Xaa_{31}$ Ser Ser Gly-Z₂, (SEQ ID NO: 43)
    Gly Gly $Xaa_{31}$ Ser Ser Gly Ala-Z₂, (SEQ ID NO: 44)
    Gly Gly $Xaa_{31}$ Ser Ser Gly Ala $Xaa_{36}$-Z₂, (SEQ ID NO: 45)
    Gly Gly $Xaa_{31}$ Ser Ser Gly Ala $Xaa_{36}$ $Xaa_{37}$-Z₂ (SEQ ID NO: 46) or
    Gly Gly $Xaa_3$, Ser Ser Gly Ala $Xaa_{36}$ $Xaa_{37}$ $Xaa_{38}$-Z₂; (SEQ ID NO: 47)
  $Xaa_{31}$, $Xaa_{36}$, $Xaa_{37}$ and $Xaa_{38}$ are independently selected from the group consisting of Pro, homoproline, thioproline and N-methylylalanine; and
  $Z_2$ is —OH or —NH₂;
  provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and pharmaceutically acceptable salts thereof.

Formula VI

Additionally, the present invention includes narrower genera of peptide compounds described in PCT Application Serial No. PCT/US98/24273, filed Nov. 13, 1998, entitled "Novel Exendin Agonist Compounds" as having particular amino acid sequences, for example, compounds of the formula [VI] [SEQ. ID. NO. 28];

```
Xaa₁ Xaa₂ Xaa₃ Xaa₅ Xaa₅ Xaa₆ Xaa₇ Xaa₈ Xaa₉ Xaa₁₀

Xaa₁₁ Xaa₁₂ Xaa₁₃ Xaa₁₄ Xaa₁₅ Xaa₁₆ Xaa₁₇ Ala

Xaa₁₉ Xaa₂₀ Xaa₂₁ Xaa₂₂ Xaa₂₃ Xaa₂₄ Xaa₂₅ Xaa₂₆

Xaa₂₇ Xaa₂₈-Z₁;
``` wherein:
  $Xaa_1$ is H is or Ala;
  $Xaa_2$ is Gly or Ala;
  $Xaa_3$ is Ala, Asp or Glu;
  $Xaa_4$ is Ala or Gly;
  $Xaa_5$ is Ala or Thr;
  $Xaa_6$ is Phe or naphthylalanine;
  $Xaa_7$ is Thr or Ser;
  $Xaa_8$ is Ala, Ser or Thr;
  $Xaa_9$ is Ala, Asp or Glu;
  $Xaa_{10}$ is Ala, Leu or pentylglycine;
  $Xaa_{11}$ is Ala or Ser;
  $Xaa_{12}$ is Ala or Lys;
  $Xaa_{13}$ is Ala or Gln;
  $Xaa_{14}$ is Ala, Leu, Met or pentylglycine;
  $Xaa_{15}$ is Ala or Glu;
  $Xaa_{16}$ is Ala or Glu;
  $Xaa_{17}$ is Ala or Glu;
  $Xaa_{19}$ is Ala or Val;
  $Xaa_{20}$ is Ala or Arg;
  $Xaa_{21}$ is Ala or Leu;
  $Xaa_{22}$ is Phe or naphthylalanine;
  $Xaa_{23}$ is Ile, Val or tert-butylglycine;
  $Xaa_{24}$ is Ala, Glu or Asp;
  $Xaa_{25}$ is Ala, Tip or Phe;
  $Xaa_{26}$ is Ala or Leu;
  $Xaa_{27}$ is Ala or Lys;
  $Xaa_{28}$ is Ala or Asn;
  $Z_1$ is —OH,
    —NH₂,
    Gly-Z₂,
    Gly Gly-Z₂
    Gly Gly $Xaa_{31}$-Z₂,
    Gly Gly $Xaa_{31}$ Ser-Z₂,
    Gly Gly $Xaa_{31}$ Ser Ser-Z₂, (SEQ ID NO: 42)
    Gly Gly $Xaa_{31}$ Ser Ser Gly-Z₂, (SEQ ID NO: 43)
    Gly Gly $Xaa_{31}$ Ser Ser Gly Ala-Z₂, (SEQ ID NO: 44)
    Gly Gly $Xaa_{31}$ Ser Ser Gly Ala $Xaa_{36}$-Z₂, (SEQ ID NO: 45)

Gly Gly Xaa$_{31}$ Ser Ser Gly Ala Xaa$_{36}$ Xaa$_{37}$-Z$_2$ (SEQ ID NO: 46)
Gly Gly Xaa$_{31}$ Ser Ser Gly Ala Xaa$_{36}$ Xaa$_{37}$ Xaa$_{38}$-Z$_2$ (SEQ ID NO: 47)
Gly Gly Xaa$_{31}$ Ser Ser Gly Ala Xaa$_{36}$ Xaa$_{37}$ Xaa$_{38}$ Ser-Z$_2$; (SEQ ID NO: 48)

Xaa$_{31}$, Xaa$_{36}$, Xaa$_{37}$ and Xaa$_{38}$ are independently Pro, homoproline, thioproline, or N-methylylalanine; and Z$_2$ is —OH or —NH$_2$;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$, and Xaa$_{28}$ are Ala; and provided that, if Xaa$_1$ is His, Arg or Tyr, then at least one of Xaa$_3$, Xaa$_4$ and Xaa$_9$ is Ala; and pharmaceutically acceptable salts thereof.

Preferred compounds of formula (VI) include those wherein Xaa$_1$ is His, Ala, Norval or 4-imidazopropionyl. Preferably, Xaa$_1$ is His, or 4-imidazopropionyl or Ala, more preferably His or 4-imidazopropionyl.

Preferred compounds of formula (VI) include those wherein Xaa2 is Gly.

Preferred compounds of formula (VI) include those wherein Xaa4 is Ala.

Preferred compounds of formula (VI) include those wherein Xaa9 is Ala.

Preferred compounds of formula (VI) include those wherein Xaa14 is Leu, pentylglycine or Met.

Preferred compounds of formula (VI) include those wherein Xaa25 is Trp or Phe.

Preferred compounds of formula (VI) include those wherein Xaa6 is Ala, Phe or naphthylalanine; Xaa22 is Phe or naphthylalanine; and Xaa23 is Ile or Val.

Preferred compounds of formula (VI) include those wherein Z1 is —NH2.

Preferred compounds of formula (VI) include those wherein Xaa31, Xaa36, Xaa37 and Xaa38 are independently selected from the group consisting of Pro, homoproline, thioproline and N-alkylalanine.

Preferred compounds of formula (VI) include those wherein Xaa39 is Ser or Tyr, preferably Ser.

Preferred compounds of formula (VI) include those wherein Z2 is —NH2.

Preferred compounds of formula (VI) include those 42 wherein Z1 is —NH2.

Preferred compounds of formula (VI) include those wherein Xaa21 is Lys-NH2-R where R is Lys, Arg, C1-C10 straight chain or branched alkanoyl.

Preferred compounds of formula (VI) include those wherein X1 is Lys Asn, Lys-NHε-R Asn, or Lys-NHε-R Ala where R is Lys, Arg, C1-C10 straight chain or branched alkanoyl. Preferred compounds of formula (VI) include those having an amino acid sequence described in PCT application Serial No. PCT/US98/24273, filed Nov. 13, 1998, entitled "Novel Exendin Agonist Compounds" as being selected from SEQ. ID. NOS. 95-110 therein.

Formula VII

Also provided are compounds described in PCT application PCT/US98/24210, filed Nov. 13, 1998, entitled "Novel Exendin Agonist Compounds", including compounds of the formula (VII) [SEQ. ID. NO. 29]:

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

X$_1$-Z$_1$;

wherein

Xaa$_1$ is His, Arg or Tyr or 4-imidazopropionyl;
Xaa$_2$ is Ser, Gly, Ala or Thr;
Xaa$_3$ is Ala, Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala, Leu or Lys-NH$^\epsilon$-R where R is Lys, Arg, C$_1$-C$_{10}$ straight chain or branched alkanoyl or cycloalkylalkanoyl;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
X$_1$ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, C$_1$-C$_{10}$ straight chain or branched alkanoyl or cycloalkylalkanoyl Z$_1$ is —OH,
—NH$_2$,
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_3$ Ser Ser-Z$_2$, (SEQ ID NO: 35)
Gly Gly Xaa$_{31}$ Ser Ser Gly-Z$_2$, (SEQ ID NO: 36)
Gly Gly Xaa$_3$ Ser Ser Gly Ala-Z$_2$, (SEQ ID NO: 37)
Gly Gly Xaa$_3$ Ser Ser Gly Ala Xaa$_{36}$-Z$_2$, (SEQ ID NO: 38)
Gly Gly Xaa$_3$ Ser Ser Gly Ala Xaa$_{36}$ Xaa$_{37}$-Z$_2$ (SEQ ID NO: 39) or
Gly Gly Xaa$_{31}$ Ser Ser Gly Ala Xaa$_{36}$ Xaa$_{37}$ Xaa$_{38}$-Z$_2$; (SEQ ID NO: 40)

Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; and Z$_2$ is —OH or —NH$_2$;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, and Xaa$_{26}$ are Ala.

Also within the scope of the present invention are pharmaceutically acceptable salts of the compound of formula (VII) and pharmaceutical compositions including said compounds and salts thereof.

Preferred exendin analogs of formula (VII) include those wherein Xaa$_1$ is His, Tyr or 4-imidazopropionyl. More preferably Xaa$_1$ is His.

Preferred are those compounds of formula (VII) wherein Xaa$_1$ is 4-imidazopropionyl.

Preferred are those compounds of formula (VII) wherein Xaa$_2$ is Gly.

Preferred compounds of formula (VII) are those wherein Xaa$_{14}$ is Leu, pentylglycine or Met.

Preferred compounds of formula (VII) are those wherein Xaa$_{25}$ is Trp or Phe.

According to one aspect, preferred are compounds of formula (VII) wherein Xaa$_6$ is Phe or naphthylalanine; and Xaa$_{22}$ is Phe or naphthylalanine; and Xaa$_{23}$ is Ile or Val. More preferably, Z$_1$ is —NH$_2$. According to one aspect, especially preferred are such compounds of formula (VII) wherein Xaa$_{31}$, Xaa$_{36}$, Xaa$_{37}$ and Xaa$_{38}$ are independently selected from the group consisting of Pro, homoproline, thioproline and N-alkylalanine. More prefers, Z$_2$ is —NH$_2$.

Preferred compounds of formula (VII) include those wherein X$_1$ is Lys Asn, Lys-NH$^\epsilon$—R Asn, or Lys-NH$^\epsilon$—R Ala where R is Lys, Arg, C$_1$-C$_{10}$ straight chain or branched alkanoyl. Preferred compounds of formula (VII) include compounds described in PCT application Serial No. PCT/US98/24210, filed Nov. 13, 1998, entitled "Novel Exendin Agonist Compounds" and identified therein as Compound Nos. 62-69.

Preferred such exendin analogs include those wherein Xaa$_1$ is His, Ala or Norval. More preferably Xaa$_1$ is His or Ala. Most preferably Xaa$_1$ is His.

Preferred are those compounds of formula (VII) wherein Xaa$_2$ is Gly.

Preferred are those compounds of formula (VII) wherein Xaa$_3$ is Ala.

Preferred are those compounds of formula (VII) wherein Xaa$_4$ is Ala.

Preferred are those compounds of formula (VII) wherein Xaa$_9$ is Ala.

Preferred are those compounds of formula (VII) wherein Xaa$_{14}$ is Leu, pentylglycine or Met.

Preferred compounds of formula (VII) are those wherein Xaa$_{25}$ is Trp or Phe.

Preferred compounds of formula (VII) are those where Xaa$_6$ is Ala, Phe or naphthylalanine; Xaa$_{22}$ is Phe or naphthylalanine; and Xaa$_{23}$ is Ile or Val.

Preferred are compounds of formula (VII) wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.

Preferably Z$_2$ is —NH$_2$.

According to one aspect, preferred are compounds of formula (VII) wherein Xaa$_1$ is Ala, His or Tyr, more preferably Ala or His; Xaa$_2$ is Ala or Gly; Xaa$_6$ is Phe or naphthylalanine; Xaa$_{14}$ is Ala, Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more preferably Ser. More preferably Z$_1$ is —NH$_2$.

According to an especially preferred aspect, especially preferred compounds include those of formula (VII) wherein: Xaa$_1$ is His or Ala; Xaa$_2$ is Gly or Ala; Xaa$_3$ is Ala, Asp or Glu; Xaa$_4$ is Ala or Gly; Xaa$_5$ is Ala or Thr; Xaa$_6$ is Phe or naphthylalanine; Xaa$_7$ is Thr or Ser; Xaa$_8$ is Ala, Ser or Thr; Xaa$_9$ is Ala, Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu, Met or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_t$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$ (SEQ ID NO: 42), Gly Gly Xaa$_{31}$ Ser Ser Gly-Z$_2$ (SEQ ID NO: 43), Gly Gly Xaa$_{31}$ Ser Ser Gly Ala-Z$_2$ (SEQ ID NO: 44), Gly Gly Xaa$_{31}$ Ser Ser Gly Ala Xaa$_{36}$-Z$_2$ (SEQ ID NO: 45), Gly Gly Xaa$_{31}$ Ser Ser Gly Ala Xaa$_{36}$ Xaa$_{37}$-Z$_2$ (SEQ ID NO: 46), Gly Gly Xaa$_{31}$ Ser Ser Gly Ala Xaa$_{36}$ Xaa$_{37}$ Xaa$_{38}$-Z$_2$ (SEQ ID NO: 47) or Gly Gly Xaa$_{31}$ Ser Ser Gly Ala Xaa$_{36}$ Xaa$_{37}$ Xaa$_{38}$ Xaa$_{39}$-Z$_2$ (SEQ ID NO: 49); Xaa$_{31}$, Xaa$_{36}$, Xaa$_{37}$ and Xaa$_{38}$ being independently Pro, homoproline, thioproline or N-methylalanine; and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and provided also that, if Xaa$_1$ is His, Arg or Tyr, then at least one of Xaa$_3$, Xaa$_4$ and Xaa$_9$ is Ala. Especially preferred compounds of formula (VII) include those described in PCT application Serial No. PCT/US98/24210, filed Nov. 13, 1998, entitled "Novel Exendin Agonist Compounds" and having the amino acid sequences identified therein as SEQ. ID. NOS. 5-93.

According to an especially preferred aspect, provided are compounds of formula (VII) where Xaa14 is Ala, Leu, Ile, Val or pentylglycine, more preferably Leu or pentylglycine, and Xaa25 is Ala, Phe, Tyr or naphthylalanine, more preferably Phe or naphthylalanine. These compounds will be less susceptible to oxidative degration, both in vitro and in vivo, as well as during synthesis of the compound.

Formula VIII

Also provided are peptide compounds described in PCT Application. Serial No. PCT/US98/24273, filed Nov. 13, 1998, entitled "Novel Exendin Agonist Compounds", including compounds of the formula (VIII) [SEQ. ID. NO. 30]:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

X$_1$-Z$_1$;

wherein

Xaa$_1$ is His, Arg, Tyr, Ala, Norval, Val, Norleu or 4-imidazopropionyl;

Xaa$_2$ is Ser, Gly, Ala or Thr;

Xaa$_3$ is Ala, Asp or Glu;

Xaa$_4$ is Ala, Norval, Val, Norleu or Gly;

Xaa$_5$ is Ala or Thr;

Xaa$_6$ is Phe, Tyr or naphthylalanine;

Xaa$_7$ is Thr or Ser;

Xaa$_8$ is Ala, Ser or Thr;

Xaa$_9$ is Ala, Norval, Val, Norleu, Asp or Glu;

Xaa$_{10}$ is Ala, Leu, Ile, Val, pentylglycine or Met;

Xaa$_{11}$ is Ala or Ser;

Xaa$_{12}$ is Ala or Lys;

Xaa$_{13}$ is Ala or Gln;

Xaa$_{14}$ is Ala, Leu, Ile, pentylglycine, Val or Met;

Xaa$_{15}$ is Ala or Glu;

Xaa$_{16}$ is Ala or Glu;

Xaa$_{17}$ is Ala or Glu;

Xaa$_{19}$ is Ala or Val;

Xaa$_{20}$ is Ala or Arg;

Xaa$_{21}$ is Ala, Leu or Lys-NH$^\epsilon$-R where R is Lys, Arg, C$^{1-10}$ straight chain or branched alkanoyl or cycloalleyl-alkanoyl;

Xaa$_{22}$ is Phe, Tyr or naphthylalanine;

Xaa$_{23}$ is Ile, Val, Leu, pentylglycine, tert-butylglycine or Met;

Xaa$_{24}$ is Ala, Glu or Asp;

Xaa$_{25}$ is Ala, Trp, Phe, Tyr or naphthylalanine;

Xaa$_{26}$ is Ala or Leu;

X$_1$ is Lys Asn, Asn Lys, Lys-NH$^\epsilon$-R Asn, Asn Lys-NH$^\epsilon$-R, Lys-NH$^\epsilon$-R Ala, Ala Lys-NH$^\epsilon$-R where R is Lys, Arg, C$_1$-C$_{10}$ straight chain or branched alkanoyl or cycloalkylalkanoyl $Z_1$ is —OH,
—NH$_2$,
Gly-$Z_2$,
Gly Gly-$Z_2$,
Gly Gly Xaa$_{31}$-$Z_2$,
Gly Gly Xaa$_{31}$ Ser-$Z_2$,
Gly Gly Xaa$_{31}$ Ser Ser-$Z_2$, (SEQ ID NO: 35)
Gly Gly Xaa$_{31}$ Ser Ser Gly-$Z_2$, (SEQ ID NO: 36)
Gly Gly Xaa$_{31}$ Ser Ser Gly Ala-$Z_2$, (SEQ ID NO: 37)
Gly Gly Xaa$_{31}$ Ser Ser Gly Ala Xaa$_{36}$-$Z_2$, (SEQ ID NO: 38)
Gly Gly Xaa$_{31}$ Ser Ser Gly Ala Xaa$_{36}$ Xaa$_{37}$-$Z_2$, (SEQ ID NO: 39)
Gly Gly Xaa$_{31}$ Ser Ser Gly Ala Xaa$_{36}$ Xaa$_{37}$ Xaa$_{38}$-$Z_2$ (SEQ ID NO: 40) or
Gly Gly Xaa$_{31}$ Ser Ser Gly Ala Xaa$_{36}$ Xaa$_{37}$ Xaa$_{38}$ Xaa$_{39}$-$Z_2$; (SEQ ID NO: 41)

Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; and $Z_2$ is —OH or —NH$_2$;

provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa17, Xaa19, Xaa$_{20}$, Xaa$_{21}$, Xaa$_{24}$, Xaa$_{25}$, Xaa$_{26}$, are Ala; and provided also that, if Xaa$_1$ is His, Arg, Tyr, or 4-imidazopropionyl then at least one of Xaa$_3$, Xaa$_4$ and Xaa$_9$ is Ala.

Preferred compounds of formula (VIII) include those wherein Xaa$_1$ is His, Ala, Norval or 4-imidazopropionyl. Preferably, Xaa$_1$ is His, or 4-imidazopropionyl or Ala, more preferably His or 4-imidazopropionyl.

Preferred compounds of formula (VIII) include those wherein Xaa$_2$ is Gly.

Preferred compounds of formula (VIII) include those wherein Xaa$_4$ is Ala.

Preferred compounds of formula (VIII) include those wherein Xaa$_9$ is Ala.

Preferred compounds of formula (VIII) include those wherein Xaa$_{14}$ is Leu, pentylglycine or Met.

Preferred compounds of formula (VIII) include those wherein Xaa$_{25}$ is Trp or Phe.

Preferred compounds of formula (VIII) include those wherein Xaa$_6$ is Ala, Phe or naphthylalanine; Xaa$_{22}$ is Phe or naphthylalanine; and Xaa$_{23}$ is Ile or Val.

Preferred compounds of formula (VIII) include those wherein $Z_1$ is —NH$_2$.

Preferred compounds of formula (VIII) include those wherein Xaa$_{31}$, Xaa$_{36}$, Xaa$_{37}$ and Xaa$_{38}$ are independently selected from the group consisting of Pro, homoproline, thioproline and N-alkylalanine.

Preferred compounds of formula (VIII) include those wherein Xaa$_{39}$ is Ser or Tyr, preferably Ser.

Preferred compounds of formula (VIII) include those wherein $Z_2$ is —NH$_2$.

Preferred compounds of formula (VIII) include those 42 wherein $Z_1$ is —NH$_2$.

Preferred compounds of formula (VIII) include those wherein Xaa$_{21}$ is Lys-NH$^\epsilon$—R where R is Lys, Arg, $C_1$-$C_{10}$ straight chain or branched alkanoyl.

Preferred compounds of formula (VIII) include those wherein $X_1$ is Lys Asn, Lys-NH$^\epsilon$—R Asn, or Lys-NH$^\epsilon$—R Ala where R is Lys, Arg, $C_1$-$C_{10}$ straight chain or branched alkanoyl.

Preferred compounds of formula (VIII) include those described in PCT Application Serial No. PCT/US98/24273, filed Nov. 13, 1998, entitled "Novel Exendin Agonist Compounds" as having an amino acid sequence selected from those identified therein as SEQ. ID. NOS. 95-110.

Formula IX

Compounds particularly useful according to the present invention are exendin analogs with agonist activity described in U.S. patent application Ser. No. 09/003,869, filed Jan. 7, 1998, entitled "Use of Exendins And Agonists Thereof For The Reduction of Food Intake", including compounds of the formula (IX) [SEQ. ID. NO:31]:

Xaa$_1$ Xaa$_2$ Xaa$_3$ Gly Thr Xaa$_4$ Xaa$_5$ Xaa$_6$ Xaa$_7$ Xaa$_8$

Ser Lys Gln Xaa$_9$ Glu Glu Glu Ala Val Arg Leu

Xaa$_{10}$ Xaa$_{11}$ Xaa$_{12}$ Xaa$_{13}$ Leu Lys Asn Gly Gly Xaa$_{14}$

Ser Ser Gly Ala Xaa$_{15}$ Xaa$_{16}$ Xaa$_{17}$ Xaa$_{18}$-Z wherein:
Xaa$_1$ is His, Arg or Tyr;
Xaa$_2$ is Ser, Gly, Ala or Thr;
Xaa$_3$ is Asp or Glu;
Xaa$_4$ is Phe, Tyr or naphthalanine;
Xaa$_5$ is Thr or Ser;
Xaa$_6$ is Ser or Thr;
Xaa$_7$ is Asp or Glu;
Xaa$_8$ is Leu, Ile, Val, pentylglycine or Met;
Xaa$_9$ is Leu, Ile, pentylglycine, Val or Met;
Xaa$_{10}$ is Phe, Tyr or naphthalanine;
Xaa$_{11}$ is Ile, Val, Leu, pentylglycine, tert-butylglycine or Met;
Xaa$_{12}$ is Glu or Asp; Xaa$_{13}$ is Trp, Phe, Tyr, or naphthalanine;
Xaa$_{14}$, Xaa$_{15}$, Xaa$_{16}$ and Xaa$_{17}$ are independently Pro, homoproline, 3Hyp, 4Hyp, thioproline, N-alkylglycine, N-alkylpentylglycine or N-alkylalanine;
Xaa$_{18}$ is Ser, Thr or Tyr; and Z is —OH or —NH$_2$;
with the proviso that the compound does not have the formula of either SEQ. ID. NOS:12 or 14. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Also useful in the present invention are pharmaceutically acceptable salts of the compounds of formula (IX).

Preferred exendin analogs include those wherein Xaa$_1$ is His or Tyr. More preferably Xaa$_1$ is His.

Preferred are those compounds wherein Xaa$_2$ is Gly.

Preferred are those compounds wherein Xaa$_9$ is Leu, pentylglycine or Met.

Preferred compounds include those wherein Xaa$_{13}$ is Trp or Phe.

Also preferred are compounds where Xaa$_4$ is Phe or naphthalanine; Xaa$_{11}$ is Ile or Val and Xaa$_{14}$, Xaa$_{15}$, Xaa$_{16}$ and Xaa$_{17}$ are independently selected from Pro, homoproline, thioproline or N-alkylalanine. Preferably N-alkylalanine has a N-alkyl group of 1 to about 6 carbon atoms.

According to an especially preferred aspect, Xaa$_{15}$, Xaa$_{16}$ and Xaa$_{17}$ are the same amino acid reside.

Preferred are compounds wherein Xaa$_{18}$ is Ser or Tyr, more preferably Ser.

Preferably Z is —NH$_2$.

According to one aspect, preferred are compounds of formula (VII) wherein Xaa$_1$ is His or Tyr, more preferably His; Xaa$_2$ is Gly; Xaa$_4$ is Phe or naphthalanine; Xaa$_9$ is Leu, pentylglycine or Met; Xaa$_{10}$ is Phe or naphthalanine; Xaa$_{11}$ is Ile or Val; Xaa$_{14}$, Xaa$_{15}$, Xaa$_{16}$ and Xaa$_{17}$ are independently selected from Pro, homoproline, thioproline or N-alkylalanine; and Xaa$_{18}$ is Ser or Tyr, more preferably Ser. More preferably Z is —NH$_2$.

According to an especially preferred aspect, especially preferred compounds include those of formula (IX) wherein: Xaa₁ is His or Arg; Xaa₂ is Gly; Xaa₃ is Asp or Glu; Xaa₄ is Phe or napthylalanine; Xaa₅ is Thr or Ser; Xaa₆ is Ser or Thr; Xaa₇ is Asp or Glu; Xaa₈ is Leu or pentylglycine; Xaa₉ is Leu or pentylglycine; Xaa₁₀ is Phe or naphthylalanine; Xaa₁₁ is Ile, Val or t-butyltylglycine; Xaa₁₂ is Glu or Asp; Xaa₁₃ is Trp or Phe; Xaa₁₄, Xaa₁₅, Xaa₁₆, and Xaa₁₇ are independently Pro, homoproline, thioproline, or N-methylalanine; Xaa₁₈ is Ser or Tyr: and Z is —OH or —NH₂; with the proviso that the compound does not have the formula of either SEQ. ID. NOS. 7 or 9. More preferably Z is —NH₂.

According to an especially preferred aspect, provided are compounds where Xaa₉ is Leu, Ile, Val or pentylglycine, more preferably Leu or pentylglycine, and Xaa₁₃ is Phe, Tyr or naphthylalanine, more preferably Phe or naphthylalanine. These compounds are believed to exhibit advantageous duration of action and to be less subject to oxidative degration, both in vitro and in vivo, as well as during synthesis of the compound.

Formula X

Also provided are compounds described in PCT Application Serial No. PCT/US98/16387, filed Aug. 6, 1998, entitled "Novel Exendin Agonist Compounds", including compounds of the formula (X) [SEQ. ID. NO:32]:

Xaa₁ Xaa₂ Xaa₃ Gly Thr Xaa₄ Xaa₅ Xaa₆ Xaa₇ Xaa₈

Ser Lys Gln Xaa₉ Glu Glu Glu Ala Val Arg Leu

Xaa₁₀ Xaa₁₁ Xaa₁₂ Xaa₁₃ Leu X₁ Gly Gly Xaa₁₄

Ser Ser Gly Ala Xaa₁₅ Xaa₁₆ Xaa₁₇ Xaa₁₈-Z wherein:
Xaa₁ is His, Arg, Tyr or 4-imidazopropionyl;
Xaa₂ is Ser, Gly, Ala or Thr;
Xaa₃ is Asp or Glu;
Xaa₄ is Phe, Tyr or naphthylalanine;
Xaa₅ is Thr or Ser;
Xaa₆ is Ser or Thr;
Xaa₇ is Asp or Glu;
Xaa₈ is Leu, Ile, Val, pentylglycine or Met;
Xaa₉ is Leu, Ile, pentylglycine, Val or Met;
Xaa₁₀ is Phe, Tyr or naphthylalanine;
Xaa₁₁ is Ile, Val, Leu, pentylglycine, tert-butylglycine or Met;
Xaa₁₂ is Glu or Asp;
Xaa₁₃ is Trp, Phe, Tyr, or naphthylalanine; X₁ is Lys Asn, Asn Lys, Lys-NH$^\epsilon$—R Asn, Asn Lys-NH$^\epsilon$—R where R is Lys, Arg, C₁-C₁₀ straight chain or branched alkanoyl or cycloalkylalkanoyl;
Xaa₁₄, Xaa₁₅, Xaa₁₆ and Xaa₁₇ are independently Pro, homoproline, 3Hyp, 4Hyp, thioproline, N-alkylglycine, N-alkylpentylglycine or N-alkylalanine;
Xaa₁₈ is Ser, Thr or Tyr; and Z is —OH or —NH₂;
with the proviso that the compound does not have the formula of either SEQ. ID. NOS. 7 or 9. Suitable compounds of formula (X) include compounds described in PCT Application Serial No. PCT/US98/16387, filed Aug. 6, 1998, entitled "Novel Exendin Agonist Compounds" having the amino acid sequences of SEQ. ID. NOS. 37-40 therein.

Preferred exendin analogs of formula (X) include those wherein Xaa₁ is His, Tyr or 4-imidazopropionyl. More preferably, Xaa₁ is His or 4-imidazopropionyl.

Preferred are those compounds of formula (X) wherein Xaa₂ is Gly.

Preferred are those compounds of formula (X) wherein Xaa₉ is Leu, pentylglycine or Met.

Preferred are those compounds of formula (X) wherein Xaa₁₃ is Trp or Phe.

Preferred are those compounds of formula (X) wherein X₁ is Lys Asn, or Lys-NH$^\epsilon$—R Asn, where R is Lys, Arg, C₁-C₁₀ straight chain or branched alkanoyl.

Also preferred are compounds of formula (X) wherein Xaa₄ is Phe or naphthylalanine; Xaa₁₀ is Phe or naphthylalanine; Xaa₁₁ is Ile or Val and Xaa₁₄, Xaa₁₅, Xaa₁₆ and Xaa₁₇ are independently selected from Pro, homoproline, thioproline or N-alkylalanine. According to an especially preferred aspect, Xaa₁₈ is Ser or Tyr. Preferred are those such compounds wherein Xaa₁₈ is Ser. Preferably, Z is —NH₂.

According to one preferred aspect, preferred are compounds of formula (X) wherein Xaa₄ is Phe or naphthylalanine; Xaa₁₀ is Phe or naphthylalanine; Xaa₁₁ is Ile or Val, X₁ is Lys Asn, or Lys-NH$^\epsilon$—R Asn, where R is Lys, Arg, C₁-C₁₀ straight chain or branched alkanoyl and Xaa₁₄, Xaa₁₅, Xaa₁₆ and Xaa₁₇ are independently selected from Pro, homoproline, thioproline or N-alkylalanine.

Exendins and exendin agonists that are peptides, such as exendin analogs, described herein may be prepared through peptide purification as described in, for example, Eng, et al., *J. Biol. Chem.* 265:20259-62, 1990; and Eng, et al., *J. Biol. Chem.* 267:7402-05, 1992, hereby incorporated by reference herein. Alternatively, exendins and exendin agonists that are peptides may be prepared by methods known to those skilled in the art, for example, as described in Raufman, et al., *J. Biol. Chem.* 267:21432-37, 1992), hereby incorporated by reference herein, using standard solid-phase peptide synthesis techniques and preferably an automated or semiautomated peptide synthesizer as previously described and is well known in the art.

Exendins and exendin agonists that are peptides may also be prepared using recombinant DNA techniques, using methods now known in the art. See, e.g., Sambrook et al., Molecular Cloning: A Laboratory Manual, 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See, e.g., Bartlett and Landen, Biorg. Chem. 14:356-377 (1986). Methods for making and/or purifying GLP-1 and its agonists, analogs, derivatives, variants, and fragments, as discussed previously, can also be utilized to make and/or purify exendins, their agonists, analogs, derivatives, variants, and fragments thereof.

The compositions of the present invention may be used in combination with a suitable pharmaceutical carrier. Such compositions comprise a therapeutically effective amount of the polypeptide, and a pharmaceutically acceptable carrier or excipient. The compositions of this invention can be administered in any effective, pharmaceutically acceptable form for warm blooded animals, including human and other animal subjects, e.g., in topical, lavage, oral, suppository, parenteral, or infusible dosage forms, as a topical, buccal, sublingual, pulmonary, or nasal spray or in any other manner effective to deliver the agents. The route of administration will preferably be designed to optimize delivery and/or localization of the agents.

In addition to the active compositions of the invention, the pharmaceutical composition may contain suitable excipients and auxiliaries that facilitate processing of the active compounds into preparations which can be used pharmaceutically. Oral dosage forms encompass tablets, capsules, granules, solutions, and suspensions. Preparations that can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, and lyophilizing processes. The processes to be used will depend ultimately on the physical properties of the active ingredient used.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances that increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions that can be dissolved or suspended in sterile water, saline, or other injectable medium prior to administration.

In addition to administration with conventional carriers, active ingredients may be administered by a variety of specialized delivery drug techniques that are known to those of skill in the art, such as portable infusion pumps.

Additional formulations for administration may be made in accordance with methods and amounts known in the art as set forth in *Remington's Pharmaceutical Sciences,* 18th Ed., Wiley Publishing (1990), the disclosure of which is herein incorporated by references in its entirety.

The compositions of the present invention can be administered along with a pharmaceutically acceptable carrier in an amount sufficient to prevent arrhythmias and/or treat an active arrhythmia. The compounds of this invention have extremely low toxicity and a low degree of side effects even at high doses. The dosing range of the compounds of this invention will vary depending on a number of factors, such as whether it is used for prophylaxis or treatment of arrhythmia, route of administration, desired dosing schedule, the physical health of the patient, etc.

Although not limited to the following ranges and provided only as an illustration, exemplary dose ranges for use in the invention can include 0.001 pmol/kg to 500 nmol/kg per day depending on the composition selected. A lower limit of a dosage range can be about 0.001 pmol/kg, 0.01 pmol/kg, 0.1 pmol/kg, 1 pmol/kg, 10 pmol/kg, or 100 pmol/kg. An upper dosage range can be about 10 pmol/kg, 100 pmol/kg, 1 nmol/kg, 10 nmol/kg, 100 nmol/kg, 250 nmol/kg or 500 nmol/kg. The desired dose will vary depending on the selected active composition. The desired dose will also depend upon other factors including the route of administration and the formulation. For example, continuous infusion as well as bolus doses and sustained release formulations are contemplated. Routes of administration include intramuscular, intravenous, subcutaneous, intradermal, transdermal, intraarticular, intrathecal and the like. Mucosal delivery is also contemplated. These routes include, but are not limited to, oral, nasal, sublingual, rectal, pulmonary and buccal routes, which may include administration of the peptide in liquid, semi-solid or solid form.

Exemplary doses for continuous infusion by intravenous (I.V.) can be about 0.1 pmol/kg/min to 10 pmol/kg/min and by subcutaneous (s.c.) about 0.1 pmol/kg/min to 75 pmol/kg/min., and for single injection (bolus) by I.V. about 0.1 nmol/kg to 2.0 nmol/kg and s.c. about 0.1 nmol/kg to 100 nmol/kg. The foregoing doses may be administered as a single dose or may be divided into multiple doses for administration. The peptides of this invention may be administered once to several times daily.

While a preferred method of administration of a GLP-1 peptide may be through a continuous application, other forms of delivery as described above are also contemplated. However, an exemplary dosing rate can be within a range of from about 1 to about 10 pmol/kg per minute of GLP-1 delivered by sustained release subcutaneous, intramuscular, interperitoneal, injected depot with sustained release, deep lung insufflation, as well as by intravenous, buccal, patch or other sustained release delivery methods. Degradation-resistant GLP-1 analogs, derivatives or variants, exendins, analogs, derivatives or variants, and other molecules of the invention need not be delivered continuously, but are suitable for bolus or sustained release dosing and may be at doses much lower than those described.

Other drugs besides compositions of the invention which are compatible with the carrier ingredients may also be incorporated into the pharmaceutical formulations. Such drugs may be readily ascertained by those of ordinary skill in the art and may include, for instance, anti-inflammatory agents, diuretics, vasodilators, etc.

It is understood that the present invention contemplates the use of not only the above-stated active forms of the compositions of the invention, but also includes the prodrugs (proforms) which metabolize to the compound and biologically active salt forms thereof, as well as optical isomers which provide the same pharmaceutical results.

The compositions of the invention may also be used in combination with agents known in the art that enhance the half-life in vivo of peptide in order to enhance or prolong the biological activity of the peptide. For example, a molecule or chemical moiety may be covalently linked to the composition of the present invention before administration thereof. Alternatively, the enhancing agent may be administered concurrently with the composition. Still further, the agent may comprise a molecule that is known to inhibit the enzymatic degradation of the compositions of the invention that may be administered concurrently with or after administration of the composition. Such a molecule may be administered, for example, orally, by injection, or any other means known in the art.

In accordance with this invention, compositions of the invention in combination with a pharmaceutically acceptable carrier are preferably administered within the first four hours following an ischemic event in order to prevent the occurrence of cardiac arrhythmia. Compositions of the invention can be co-administered with glucose (5%) if required to maintain blood glucose levels $\geq 5$ mM (to maintain efficient insulin secretion). Similarly, co-administration of potassium ($K^+$) may be considered, depending on the extent to which activation of the membrane $Na^+/K^-$ ATPase leads to a shift of $K^+$ into the intracellular space.

With respect to reperfusion, treatment with compositions of the invention should be commenced concurrently or as soon as possible following therapies that reestablish flow in an artery that was obstructed by a blood clot (e.g., thrombolytic therapy) or other obstructive materials, or following an intervention, such as angioplasty, coronary bypass grafting, or placement of an intracoronary stent. Therapy should continue thereafter. In the case of cardiac surgery, the treatment should preferably commence 12-24 hours prior to surgery, during surgery from the onset of anesthesia until aortic crossclamping, and immediately after unclamping for a period of at least 72 hours postoperatively. As earlier explained, co-administration of a free radical scavenger or antioxidants will further aid reperfusion recovery.

What is claimed is:

1. A method for treating arrhythmias comprising:
administering to an individual in need of such treatment an amount of a composition effective to treat arrhythmias, said composition comprising an exendin or exendin analog of SEQ ID NO: 25 or SEQ ID NO: 26 that binds to a receptor for GLP-1; and
thereby treating said arrhythmias.

2. The method of claim 1 wherein the exendin or exendin analog is SEQ ID NO: 14 or 19-24.

3. The method of claim 1 wherein the composition is administered in a dose of from about 0.01 pmol/kg to 20 nmol/kg.

4. The method of claim 1 wherein the composition is administered concurrently with a member of the group consisting of: glucose, potassium, and a free radical scavenger.

5. The method of claim 1 wherein the composition is administered within four hours of an ischemic event.

6. The method of claim 5 wherein the composition continues to be administered following the ischemic event.

7. The method of claim 1 wherein the composition is administered concurrently or as soon as possible following therapies that reestablish flow in an artery that has been obstructed.

8. The method of claim 1 wherein the composition is administered to treat ventricular arrhythmias.

9. The method of claim 8 wherein the ventricular arrhythmia is caused by a condition selected from the group consisting of cardiac ischemia, cardiac ischemia-reperfusion, and congestive heart failure.

10. The method of claim 2 wherein the exendin or exendin analog is SEQ ID NO: 14.

11. The method of claim 2 wherein the exendin or exendin analog is SEQ ID NO: 19.

12. The method of claim 2 wherein the exendin or exendin analog is SEQ ID NO: 20.

13. The method of claim 2 wherein the exendin or exendin analog is SEQ ID NO: 21.

14. The method of claim 2 wherein the exendin or exendin analog is SEQ ID NO: 22.

15. The method of claim 2 wherein the exendin or exendin analog is SEQ ID NO: 23.

16. The method of claim 2 wherein the exendin or exendin analog is SEQ ID NO: 24.

17. A method for treating arrhythmias comprising:
administering to an individual in need of such treatment an amount of a composition effective to treat arrhythmias, said composition comprising exendin-4; and
thereby treating said arrhythmias.

* * * * *